(12) United States Patent
Peluso

(10) Patent No.: US 8,252,532 B2
(45) Date of Patent: Aug. 28, 2012

(54) REGULATORS OF THE NON-GENOMIC ACTION OF PROGESTERONE AND METHODS OF USE

(75) Inventor: John J. Peluso, Avon, CT (US)

(73) Assignee: University of Connecticut, Farmington, CT (US)

( * ) Notice: Subject to any disclaimer, the term of this patent is extended or adjusted under 35 U.S.C. 154(b) by 530 days.

(21) Appl. No.: 12/380,789

(22) Filed: Mar. 4, 2009

(65) Prior Publication Data
US 2009/0226917 A1 Sep. 10, 2009

Related U.S. Application Data

(63) Continuation-in-part of application No. 11/732,780, filed on Apr. 4, 2007, now Pat. No. 7,723,300.

(60) Provisional application No. 60/789,301, filed on Apr. 5, 2006.

(51) Int. Cl.
*C12Q 1/68* (2006.01)
*C12Q 1/00* (2006.01)
(52) U.S. Cl. ............... 435/6.1; 435/4; 435/7.8
(58) Field of Classification Search .......... None
See application file for complete search history.

(56) References Cited

U.S. PATENT DOCUMENTS

| | | | |
|---|---|---|---|
| 5,976,837 A | 11/1999 | Jacobs et al. | |
| 2004/0138187 A1* | 7/2004 | Reading et al. | ............... 514/169 |
| 2005/0033018 A1 | 2/2005 | Lal et al. | |
| 2005/0074842 A1 | 4/2005 | Kato et al. | |
| 2007/0238645 A1 | 10/2007 | Peluso | |

OTHER PUBLICATIONS

"Designing Your Custom Peptides", from SIGMA GENOSYS,. Accessed Dec. 16, 2004, pp. 1-2.
Barnes, Mack N. et al., "A Pilot Study of Ovarian Cancer Chemoprevention Using Medroxyprogesterone Acetate in an Avian Model of Spontaneous Ovarian Carcinogenesis", Gynecologic Oncology 2002 , 87, 57-63.
Berendsen, J. J. "A Glimpse of the Holy Grail?", Science Oct. 23, 1998 , 282:642-643.
Bradley, Christina M. et al., "Limits of Cooperativity in a Structurally Modular Protein: Response of the Notch Ankyrin Domain to", Journal of Molecular Biology 2002 , 324:373-386.
Cameron, Mark R. et al., "The Steroidogenic and Morphological Effects of Paclitaxel on Cultured Ovarian Cancer Cells", Oncology Research 1995 , vol. 7, Nos. 3/4, pp. 145-156.
Chaffkin, L. M. et al., "Progesterone as an Autocrine/Paracrine Regulator of Human Granulosa Cell Proliferation", Journal of Clinical Endrocrinology and Metabolism 1992 , vol. 75, No. 6, pp. 1404-1408.
Chaffkin, L. M. et al., "The Role of Progesterone in Regulating Human Granulosa Cell Proliferation adn Differentiation in vitro", Journal of Clinical Endocrinology and Metabolism 1993 , vol. 76, No. 3, pp. 696-700.

Chen, Xiaojun et al., "Effect of progesterone combined with chemotherapy of epithelial ovarian cancer", Chinese Medical Journal 2003 , 116: 388-91.
Crudden, Gerard et al., "Hpr6 (Heme-1 Domain Protein) Regulates the Susceptibility of Cancer Cells to Chemotherapeutic Drugs", The Journal of Pharmacology and Experimental Therapeutics 2006 , vol. 316, No. 1, 448-455.
Crudden, Gerard et al., "Overexpression of the Cytochrome P450 Activator Hpr6 (Heme-1 Domain Protein/Human Progesterone Receptor) in Tumors", Tumor Biol 2005 , 26:142-146.
Davis, Michael et al., "Refine of Two Chromosome 11q Regions of Loss of Heterozygosity in Ovarian Cancer", Cancer Research Feb. 15, 1996 , 56, 741-744.
Engmann, Lawrence et al., "Progesterone Regulation of Human Granulosa/Luteal Cell Viability by an RU486-Independent Mechanism", The Journal of Clinical Endocrinology & Metabolism 2006 , 91(12:4962-4968.
Gabra, H. et al., "Chromosome 11 allele imbalance and clinicopathological correlates in ovarian tumours", British Journal of Cancer 1995 , 72:367-375.
Gabra, Hani et al., "Loss of Heterozygosity at 11q22 Correlates with Low Progestereone Receptor Content in Epithelial Ovarian Cancer", Clinical Cancer Research Sep. 1995 , vol. 1, 945-953.
Hempling, R. E. et al., "Progesterone Receptor Status Is a Significant Prognostic Variable of Progression-Free Survival in Advanced Epithelial Ovarian Cancer", J. Clin. Oncol 1998 , 21(5): 447-451.
Ho, Shuk-Mei "Estrogen, Progesterone and Epithelial Ovarian Cancer", Reproductive Biology and Endocrinology 2003 , 1:73.
Juengel, J. L. et al., "Molecular regulation of luteal progesterone synthesis in domestic ruminants", Journal of Reproduction and Fertility Supplement 1999 , 54: 193-205.
Kim, Ki-Yon et al., "Type II Gonadotropin-Releasing Hormone Stimulates p38 Mitogen-Activated Protein Kinase and Apoptosis in Ovarian Cancer Cells", The Journal of Clinical Endocrinology & Metabolism 2004 , 89:(6):3020-3026.
Lindgren, Peter et al., "Steroid receptors and hormones in relation to cell proliferation and apoptosis in poorly differentiated epithelial ovarian tumors", International Journal of Oncology 2001 , 19: 31-38.
Losel, R et al., "Classic and Non-classic Progesterone Receptors are both Expressed in Human Spermatozoa", Cancer Epidemiol Biomarkers Prev 2005 , 14(1).
Lukanova, Annekatrin et al., "Endogenous Hormones and Ovarian Cancer: Epidemiology and Current Hypotheses", Cancer Epidemiol Biomarkers Prev 2005 , 14(1). McDonnel, Anna C. et al., "Effects of progesterone on ovarian tumorigenesis in xenografted mice", Cancer Letters 2005 , 221:49-53.
Munstedt, Karsten et al., "Steroid Hormone Receptors and Long Term Survival in Invasive Ovarian Cancer", Cancer Oct. 15, 2000 , vol. 89, No. 8, 1783-1791.
Ngo, et al., ""Computational Complexity, Protein Structure Prediction, and the Levinthal Paradox,"", The Protein Folding Problem and tertiary Structure Prediction, K. Merc, Jr. and S. Le Grand Edition, 1994 , pp. 491-495.

(Continued)

*Primary Examiner* — Julie Ha
(74) *Attorney, Agent, or Firm* — Kilpatrick Townsend & Stockton LLP

(57) ABSTRACT

A progesterone regulator capable of modulating the non-genomic action of progesterone and methods of using the progesterone regulator are described. The progesterone regulator is useful for attenuating progesterone's inhibition of apoptosis and for the treatment of patients having a progesterone-responsive tissue disease such as endometriosis or cancer, particularly ovarian cancer, as well as for diagnosis, prognosis, and/or staging of ovarian cancers.

5 Claims, 15 Drawing Sheets
(9 of 15 Drawing Sheet(s) Filed in Color)

OTHER PUBLICATIONS

Peluso, John J. et al., "Expression and Function of PAIRBP1 Within Gonadotropin-Primed Immature Rat Ovaries: PAIRBP1 Regulation of Granulosa and Luteal Cell Viability", Biology of Reproduction 2005, 73, 261-270.

Peluso, J. J. et al., "Involvement of an Unnamed Protein, RDA288, in the Mechanism through which Progesterone Mediates Its Antiapoptotoc Action in Spontaneously Immortalized Granulosa Cells", Endroncrinology 2004, 145(6):3014-3022.

Peluso, John J. et al., "Multiplicity of Progesterone's Actions and Receptors in the Mammalian Ovary", Biology of Reproduction 2006, 75, 2-8.

Peluso, John J. et al., "Progesterone Membrane Receptor Component 1 Expression in the Immature Rat Ovary and its Role in Mediating Progesterone's Antiapoptotic Action", Endocrinology 2006, 417(6):3133-3140.

Peluso, John J. et al., "Progesterone Receptor Membrane Component-1 (PGRMC1) is the Mediator of Progesterone's Antiapoptotic Action in Spontaneously Immortalized Granulosa Cells as Revealed by PGRMC1 Small Interfering Ribonucleic Acid Treatment and Functional Analysis of PGRMC1 Mu", Endocrinology Feb. 2008, 149(2):534-543.

Peluso, John J. et al., "Regulation of Ovarian Cancer Cell Viability and Sensitivity to Cisplatin by Progesterone Receptor Membrane Component-1", J Clin Endocrinol Metab May 2008, 93(5):1592-1599.

Rae, Michael T. et al., "Steroid signalling in the ovarian surface epithelium", Trends in Endocrinology and Metabolism Sep. 2005, vol. 16, No. 7, 327-333.

Rodriguez, Gustavo C. et al., "Effect of Progestin on the Ovarian Epithelium of Macaques: Cancer Prevention Through Apoptosis?", J. Soc. Gynecol. Investig. 1998, 5:271-276.

Rudinger, J. ""Characteristics of the amino acids as components of a peptide hormone sequence,"", Peptide Hormones,JA Parsons Edition, University Park Press,, Jun. 1976, pp. 1-7.

Salzberg, Marc et al., "Current Concepts of Treatment Strategies in Advanced or Recurrent Ovarian Cancer", Oncology 2005, I8:293-298.

Schinzel, R. et al., ""The phosphate recognition site of *Escherichia coli* maltodextrin phosphorylase,"", FEBS Jul. 1991, 286(1,2):125-128.

Skolnick, et al., "From genes to protein structure and function: novel applications of computational approached in the", Trends in Biotechnology 2000, 18(1):34-39.

Slotman, Berend J. et al., "Survival of Patients with Ovarian Cancer Apart from Stage and Grade, Tumor Progesterone Receptor Content is a Prognostic Indicator", Cancer 1990, 66:740-744.

Voet, Donald et al., "Biochemistry", John Wiley & Sons, Inc. 1995, Second Edition, 235-241.

Yu, Sunhee et al., "Apoptosis Induced by Progesterone in Human Ovarian Cancer Cell Line SNU-840", Journal of Cellular Biochemistry 2001, 82:445-451.

\* cited by examiner

SEQUENCE LISTING

```
<160> NUMBER OF SEQ ID NOS: 20

<210> SEQ ID NO 1
<211> LENGTH: 20
<212> TYPE: PRT
<213> ORGANISM: Homo sapiens

<400> SEQUENCE: 1

Met Ala Ala Glu Asp Val Val Ala Thr Gly Ala Asp Pro Ser Glu Leu
1               5                   10                  15

Glu Leu Leu Leu
            20

<210> SEQ ID NO 2
<211> LENGTH: 20
<212> TYPE: PRT
<213> ORGANISM: Homo sapiens

<400> SEQUENCE: 2

Met Ala Ala Glu Asp Val Val Ala Thr Gly Ala Asp Pro Ser Asp Leu
1               5                   10                  15
```

```
Glu Ser Gly Gly
        20

<210> SEQ ID NO 3
<211> LENGTH: 195
<212> TYPE: PRT
<213> ORGANISM: Homo sapiens

<400> SEQUENCE: 3

Met Ala Ala Glu Asp Val Val Ala Thr Gly Ala Asp Pro Ser Asp Leu
1               5                   10                  15

Glu Ser Gly Gly Leu Leu His Glu Ile Phe Thr Ser Pro Leu Asn Leu
            20                  25                  30

Leu Leu Leu Gly Leu Cys Ile Phe Leu Leu Tyr Lys Ile Val Arg Gly
        35                  40                  45

Asp Gln Pro Ala Ala Ser Gly Asp Ser Asp Asp Glu Pro Pro Pro
    50                  55                  60

Leu Pro Arg Leu Lys Arg Arg Asp Phe Thr Pro Ala Glu Leu Arg Arg
65                  70                  75                  80

Phe Asp Gly Val Gln Asp Pro Arg Ile Leu Met Ala Ile Asn Gly Lys
                85                  90                  95

Val Phe Asp Val Thr Lys Gly Arg Lys Phe Tyr Gly Pro Glu Gly Pro
            100                 105                 110

Tyr Gly Val Phe Ala Gly Arg Asp Ala Ser Arg Gly Leu Ala Thr Phe
        115                 120                 125

Cys Leu Asp Lys Glu Ala Leu Lys Asp Glu Tyr Asp Asp Leu Ser Asp
    130                 135                 140

Leu Thr Ala Ala Gln Gln Glu Thr Leu Ser Asp Trp Glu Ser Gln Phe
145                 150                 155                 160

Thr Phe Lys Tyr His His Val Gly Lys Leu Leu Lys Glu Gly Glu Glu
                165                 170                 175

Pro Thr Val Tyr Ser Asp Glu Glu Pro Lys Asp Gly Ser Ala Arg
            180                 185                 190

Lys Asn Asp
        195

<210> SEQ ID NO 4
<211> LENGTH: 588
<212> TYPE: DNA
<213> ORGANISM: Homo sapiens

<400> SEQUENCE: 4
atggctgccg aggatgtggt ggcgactggc gccgacccaa gcgatctgga gagcggcggg    60
ctgctgcatg agattttcac gtcgccgctc aacctgctgc tgcttggcct ctgcatcttc    120
ctgctctaca gatcgtgcg cggggaccag ccggcggcca gcggcgacag cgacgacgac    180
gagccgcccc ctctgccccg cctcaagcgg cgcgacttca cccccgccga gctgcggcgc    240
ttcgacggcg tccaggaccc gcgcatactc atggccatca acggcaaggt gttcgatgtg    300
accaaaggcc gcaaattcta cgggcccgag gggccgtatg gggtctttgc tggaagagat    360
gcatccaggg gccttgccac attttgcctg gataaggaag cactgaagga tgagtacgat    420
gacctttctg acctcactgc tgcccagcag gagactctga gtgactggga gtctcagttc    480
actttcaagt atcatcacgt gggcaaactg ctgaaggagg gggaggagcc cactgtgtac    540
tcagatgagg aagaaccaaa agatgagagt gcccggaaaa atgattaa              588

<210> SEQ ID NO 5
```

```
<211> LENGTH: 933
<212> TYPE: PRT
<213> ORGANISM: Homo sapiens

<400> SEQUENCE: 5

Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
            20                  25                  30

Ala Gly Pro Phe Pro Gly Ser Gln Thr Ser Asp Thr Leu Pro Glu Val
        35                  40                  45

Ser Ala Ile Pro Ile Ser Leu Asp Gly Leu Leu Phe Pro Arg Pro Cys
50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
210                 215                 220

Asp Gly Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Val
                245                 250                 255

Pro Pro Gly Ala Ala Ala Gly Gly Val Ala Leu Val Pro Lys Glu Asp
            260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Ser Ser Pro Cys Ala Ser Ser Thr Pro
            340                 345                 350

Val Ala Val Gly Asp Phe Pro Asp Cys Ala Tyr Pro Pro Asp Ala Glu
        355                 360                 365

Pro Lys Asp Asp Ala Tyr Pro Leu Tyr Ser Asp Phe Gln Pro Pro Ala
370                 375                 380

Leu Lys Ile Lys Glu Glu Glu Glu Gly Ala Glu Ala Ser Ala Arg Ser
385                 390                 395                 400
```

-continued

```
Pro Arg Ser Tyr Leu Val Ala Gly Ala Asn Pro Ala Ala Phe Pro Asp
            405                 410                 415
Phe Pro Leu Gly Pro Pro Pro Leu Pro Arg Ala Thr Pro Ser
            420             425                 430
Arg Pro Gly Glu Ala Ala Val Thr Ala Ala Pro Ala Ser Ala Ser Val
            435                 440                 445
Ser Ser Ala Ser Ser Ser Gly Ser Thr Leu Glu Cys Ile Leu Tyr Lys
450                 455                 460
Ala Glu Gly Ala Pro Pro Gln Gln Gly Pro Phe Ala Pro Pro Pro Cys
465                 470                 475                 480
Lys Ala Pro Gly Ala Ser Gly Cys Leu Leu Pro Arg Asp Gly Leu Pro
                485                 490                 495
Ser Thr Ser Ala Ser Ala Ala Ala Gly Ala Ala Pro Ala Leu Tyr
            500                 505                 510
Pro Ala Leu Gly Leu Asn Gly Leu Pro Gln Leu Gly Tyr Gln Ala Ala
            515                 520                 525
Val Leu Lys Glu Gly Leu Pro Gln Val Tyr Pro Pro Tyr Leu Asn Tyr
530                 535                 540
Leu Arg Pro Asp Ser Glu Ala Ser Gln Ser Pro Gln Tyr Ser Phe Glu
545                 550                 555                 560
Ser Leu Pro Gln Lys Ile Cys Leu Ile Cys Gly Asp Glu Ala Ser Gly
                565                 570                 575
Cys His Tyr Gly Val Leu Thr Cys Gly Ser Cys Lys Val Phe Phe Lys
            580                 585                 590
Arg Ala Met Glu Gly Gln His Asn Tyr Leu Cys Ala Gly Arg Asn Asp
            595                 600                 605
Cys Ile Val Asp Lys Ile Arg Arg Lys Asn Cys Pro Ala Cys Arg Leu
610                 615                 620
Arg Lys Cys Cys Gln Ala Gly Met Val Leu Gly Gly Arg Lys Phe Lys
625                 630                 635                 640
Lys Phe Asn Lys Val Arg Val Arg Ala Leu Asp Ala Val Ala Leu
                645                 650                 655
Pro Gln Pro Val Gly Val Pro Asn Glu Ser Gln Ala Leu Ser Gln Arg
            660                 665                 670
Phe Thr Phe Ser Pro Gly Gln Asp Ile Gln Leu Ile Pro Pro Leu Ile
            675                 680                 685
Asn Leu Leu Met Ser Ile Glu Pro Asp Val Ile Tyr Ala Gly His Asp
            690                 695                 700
Asn Thr Lys Pro Asp Thr Ser Ser Ser Leu Leu Thr Ser Leu Asn Gln
705                 710                 715                 720
Leu Gly Glu Arg Gln Leu Leu Ser Val Val Lys Trp Ser Lys Ser Leu
                725                 730                 735
Pro Gly Phe Arg Asn Leu His Ile Asp Asp Gln Ile Thr Leu Ile Gln
            740                 745                 750
Tyr Ser Trp Met Ser Leu Met Val Phe Gly Leu Gly Trp Arg Ser Tyr
            755                 760                 765
Lys His Val Ser Gly Gln Met Leu Tyr Phe Ala Pro Asp Leu Ile Leu
            770                 775                 780
Asn Glu Gln Arg Met Lys Glu Ser Ser Phe Tyr Ser Leu Cys Leu Thr
785                 790                 795                 800
Met Trp Gln Ile Pro Gln Glu Phe Val Lys Leu Gln Val Ser Gln Glu
                805                 810                 815
Glu Phe Leu Cys Met Lys Val Leu Leu Leu Leu Asn Thr Ile Pro Leu
```

```
                    820             825             830
Glu Gly Leu Arg Ser Gln Thr Gln Phe Glu Glu Met Arg Ser Ser Tyr
            835                 840                 845

Ile Arg Glu Leu Ile Lys Ala Ile Gly Leu Arg Gln Lys Gly Val Val
        850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
        915                 920                 925

Leu Phe His Lys Lys
    930

<210> SEQ ID NO 6
<211> LENGTH: 13037
<212> TYPE: DNA
<213> ORGANISM: Homo sapiens

<400> SEQUENCE: 6
agtccacagc tgtcactaat cggggtaagc cttgttgtat tgtgcgtgt gggtggcatt        60 ctcaatgaga actagcttca cttgtcattt gagtgaaatc tacaacccga ggcggctagt      120
gctcccgcac tactgggatc tgagatcttc ggagatgact gtcgcccgca gtacggagcc      180
agcagaagtc cgacccttcc tgggaatggg ctgtaccgag aggtccgact agccccaggg      240
ttttagtgag ggggcagtgg aactcagcga gggactgaga gcttcacagc atgcacgagt      300
ttgatgccag agaaaaagtc gggagataaa ggagccgcgt gtcactaaat tgccgtcgca      360
gccgcagcca ctcaagtgcc ggacttgtga gtactctgcg tctccagtcc tcggacagaa      420
gttggagaac tctcttggag aactccccga gttaggagac gagatctcct aacaattact      480 acttttctt gcgctcccca cttgccgctc gctgggacaa acgacagcca cagttcccct       540
gacgacagga tggaggccaa gggcaggagc tgaccagcgc cgccctcccc cgccccgac      600 ccaggaggtg gagatccctc cggtccagcc acattcaaca cccactttct cctccctctg      660
cccctatatt cccgaaaccc cctcctcctt ccctttccc tcctcctgga gacgggggag       720
gagaaagggg gagtccagtc gtcatgactg agctgaaggc aaagggtccc cgggctcccc      780
acgtggcggg cggcccgccc tcccccgagg tcggatcccc actgctgtgt cgcccagccg      840
caggtccgtt cccggggagc cagacctcgg acaccttgcc tgaagtttcg gccatacca      900 tctccctgga cgggctactc ttccctcggc cctgccaggg acaggacccc tccgacgaaa      960
agacgcagga ccagcagtcg ctgtcggacg tggagggcgc atattccaga gctgaagcta     1020 caagggtgc tggaggcagc agttctagtc ccccagaaaa ggacagcgga ctgctggaca     1080
gtgtcttgga cactctgttg gcgccctcag gtcccgggca gagccaaccc agccctcccg     1140
cctgcgaggt caccagctct tggtgcctgt ttggccccga acttcccgaa gatccaccgg     1200
ctgcccccgc cacccagcgg gtgttgtccc cgctcatgag ccggtccggg tgcaaggttg     1260
gagacagctc cgggacggca gctgcccata aagtgctgcc ccggggcctg tcaccagccc     1320
ggcagctgct gctcccggcc tctgagagcc tcactggtc cggggccccca gtgaagccgt     1380 ctccgcaggc cgctgcggtg gaggttgagg aggaggatgg ctctgagtcc gaggagtctg     1440
cgggtccgct tctgaagggc aaacctcggg ctctgggtgg cgcggcggct ggaggaggag     1500
```

```
ccgcggctgt cccgccgggg gcggcagcag gaggcgtcgc cctggtcccc aaggaagatt    1560
cccgcttctc agcgcccagg gtcgccctgg tggagcagga cgcgccgatg gcgcccgggc    1620
gctccccgct ggccaccacg gtgatggatt tcatccacgt gcctatcctg cctctcaatc    1680
acgccttatt ggcagcccgc actcggcagc tgctggaaga cgaaagttac gacggcgggg    1740
ccggggctgc cagcgccttt gccccgccgc ggagttcacc ctgtgcctcg tccaccccgg    1800
tcgctgtagg cgacttcccc gactgcgcgt acccgcccga cgccgagccc aaggacgacg    1860
cgtaccctct ctatagcgac ttccagccgc ccgctctaaa gataaaggag gaggaggaag    1920
gcgcggaggc ctccgcgcgc tccccgcgtt cctaccttgt ggccggtgcc aaccccgcag    1980
ccttcccgga tttcccgttg gggccaccgc cccgctgcc gccgcgagcg acccatcca     2040 gacccgggga agcggcggtg acggccgcac ccgccagtgc ctcagtctcg tctgcgtcct    2100
cctcggggtc gaccctggag tgcatcctgt acaaagcgga gggcgcgccg cccagcagg    2160 gcccgttcgc gccgccgccc tgcaaggcgc cgggcgcgag cggctgcctg ctcccgcggg    2220
acggcctgcc ctccacctcc gcctctgccg ccgccgccgg gcggccccc gcgctctacc     2280 ctgcactcgg cctcaacggg ctcccgcagc tcggctacca ggccgccgtg ctcaaggagg    2340
gcctgccgca ggtctacccg ccctatctca actacctgag gccggattca gaagccagcc    2400
agagcccaca atacagcttc gagtcattac ctcagaagat ttgtttaatc tgtggggatg    2460
aagcatcagg ctgtcattat ggtgtcctta cctgtgggag ctgtaaggtc ttctttaaga    2520
gggcaatgga agggcagcac aactacttat gtgctggaaa aaatgactgc atcgttgata    2580
aaatccgcag aaaaaactgc ccagcatgtc gccttagaaa gtgctgtcag gctggcatgg    2640
tccttggagg tcgaaaattt aaaaagttca ataaagtcag agttgtgaga gcactggatg    2700
ctgttgctct cccacagcca gtgggcgttc caaatgaaag ccaagcccta gccagagat    2760 tcactttttc accaggtcaa gacatacagt tgattccacc actgatcaac ctgttaatga    2820
gcattgaacc agatgtgatc tatgcaggac atgacaacac aaaacctgac acctccagtt    2880
ctttgctgac aagtcttaat caactaggcg agaggcaact tctttcagta gtcaagtggt    2940
ctaaatcatt gccaggtttt cgaaacttac atattgatga ccagataact ctcattcagt    3000
attcttggat gagcttaatg gtgtttggtc taggatggag atcctacaaa cacgtcagtg    3060
ggcagatgct gtattttgca cctgatctaa tactaaatga acagcggatg aaagaatcat    3120
cattctattc attatgcctt accatgtggc agatcccaca ggagtttgtc aagcttcaag    3180
ttagccaaga agagttcctc tgtatgaaag tattgttact tcttaataca attcctttgg    3240
aagggctacg aagtcaaacc cagtttgagg agatgaggtc aagctacatt agagagctca    3300
tcaaggcaat tggtttgagg caaaaggag ttgtgtcgag ctcacagcgt ttctatcaac    3360
ttacaaaact tcttgataac ttgcatgatc ttgtcaaaca acttcatctg tactgcttga    3420
atacatttat ccagtcccgg gcactgagtg ttgaatttcc agaaatgatg tctgaagtta    3480
ttgctgcaca attacccaag atattggcag ggatggtgaa accccttctc tttcataaaa    3540
agtgaatgtc atcttttttct tttaaagaat taaattttgt ggtatgtctt tttgttttgg    3600
tcaggattat gaggtcttga gttttttataa tgttcttctg aaagccttac atttataaca    3660
tcatagtgtg taaatttaaa agaaaaattg tgaggttcta attattttct tttataaagt    3720
ataattagaa tgtttaactg ttttgtttac ccatattttc ttgaagaatt tacaagattg    3780
aaaaagtact aaaattgtta aagtaaacta tcttatccat attatttcat accatgtagg    3840
tgaggatttt taacttttgc atctaacaaa tcatcgactt aagagaaaaa atcttacatg    3900
```

```
taataacaca aagctattat atgttatttc taggtaactc cctttgtgtc aattatattt    3960
ccaaaaatga acctttaaaa tggtatgcaa aattttgtct atatatattt gtgtgaggag    4020
gaaattcata actttcctca gattttcaaa agtatttta atgcaaaaaa tgtagaaaga    4080
gtttaaaacc actaaaatag attgatgttc ttcaaactag gcaaacaac tcatatgtta    4140 agaccatttt ccagattgga aacacaaatc tcttaggaag ttaataagta gattcatatc    4200
attatgcaaa tagtattgtg ggttttgtag gttttttaaaa taaccttttt tggggagaga    4260
attgtcctct aatgaggtat tgcgagtgga cataagaaat cagaagatta tggcctaact    4320
gtactcctta ccaactgtgg catgctgaaa gttagtcact cttactgatt ctcaattctc    4380
tcacctttga aagtagtaaa atatctttcc tgccaattgc tcctttgggt cagagcttat    4440
taacatcttt tcaaatcaaa ggaaagaaga aagggagagg aggaggaggg aggtatcaat    4500
tcacatacct ttctcctctt tatcctccac tatcatgaat tcatattatg tttcagccat    4560
gcaaatcttt ttaccatgaa atttcttcca gaattttccc cctttgacac aaattccatg    4620
catgtttcaa ccttcgagac tcagccaaat gtcatttctg taaaatcttc cctgagtctt    4680
ccaagcagta atttgccttc tcctagagtt tacctgccat tttgtgcaca tttgagttac    4740
agtagcatgt tattttacaa ttgtgactct cctgggagtc tgggagccat ataaagtggt    4800
caatagtgtt tgctgactga gagttgaatg acattttctc tctgtcttgg tattactgta    4860
gatttcgatc attctttggt tacatttctg catatttctg tacccatgac tttatcactt    4920
tcttctccca tgctttatct ccatcaatta tcttcattac ttttaaattt tccacctttg    4980
cttcctactt tgtgagatct ctcccttttac tgactataac atagaagaat agaagtgtat    5040
tttatgtgtc ttaaggacaa tactttagat tccttgttct aagtttttaa actgaatgaa    5100
tggaatatta tttctctccc taagcaaaat tccacaaaac aattatttct tatgtttatg    5160
tagccttaaa ttgttttgta ctgtaaacct cagcataaaa actttcttca tttctaattt    5220
cattcaacaa atattgattg aatacctggt attagcacaa gaaaaatgtg ctaataagcc    5280
ttatgagaat ttggagctga agaaagacat ataactcagg aaagttacag tccagtagta    5340
ggtataaatt acagtgcctg ataaataggc attttaatat ttgtacactc aacgtatact    5400
aggtaggtgc aaaacattta catataattt tactgatacc catgcagcac aaaggtacta    5460
actttaaata ttaaataaca cctttatgtg tcagtaattc atttgcatta aatcttattg    5520
aaaaggcttt caatatattt tccccacaaa tgtcatccca agaaaaaagt attttttaaca    5580 tctcccaaat ataatagtta caggaaatct acctctgtga gagtgacacc tctcagaatg    5640
aactgtgtga cacaagaaaa tgaatgtagg tctatccaaa aaaaacccca agaaacaaaa    5700
acaatattat tagccccttta tgcttaagtg atggactcag ggaacagttg atgttgtgat    5760
cattttatta tctgattctt gttactttga attaaaccaa tattttgatg atataaatca    5820
tttccaccag catatattta atttccataa taactttaaa attttctaat ttcactcaac    5880
tatgagggaa tagaatgtgg tggccacagg tttggctttt gttaaaatgt ttgatatctt    5940
cgatgttgat ctctgtctgc aatgtagatg tctaaacact aggatttaat atttaaggct    6000
aagctttaaa aataaagtac ctttttaaaa agaatatggc ttcaccaaat ggaaaatacc    6060
taatttctaa atcttttttct ctacaaagtc ctatctacta atgtctccat tactatttag    6120
tcatcataac cattatcttc attttacatg tcgtgttctt tctggtagct ctaaaatgac    6180
actaaatcat aagaagacag gttacatatc aggaaatact tgaaggttac tgaaatagat    6240
tcttgagtta atgaaaatat tttctgtaaa aaggtttgaa aagccatttg agtctaaagc    6300
```

```
attatacctc cattatcagt agttatgtga caattgtgtg tgtgtttaat gtttaaagat    6360
gtggcacttt ttaataaggc aatgctatgc tattttttcc catttaacat taagataatt    6420
tattgctata cagatgatat ggaaatatga tgaacaatat ttttttttgcc aaaactatgc    6480 cttgtaagta gccatggaat gtcaacctgt aacttaaatt atccacagat agtcatgtgt    6540
ttgatgatgg gcactgtgga gataactgac ataggactgt gccccccttc tctgccactt    6600
actagctgga tgagattaag caagtcattt aactgctctg attaaacctg cctttcccaa    6660
gtgctttgta atgaatagaa atggaaacca aaaaaaacgt atacaggcct tcagaaatag    6720
taattgctac tattttgttt tcattaagcc atagttctgg ctataatttt atcaaactca    6780
ccagctatat tctacagtga aagcaggatt ctagaaagtc tcactgtttt atttatgtca    6840
ccatgtgcta tgatatattt ggttgaattc atttgaaatt agggctggaa gtattcaagt    6900
aatttcttct gctgaaaaaa tacagtgttt tgagtttagg gcctgtttta tcaaagttct    6960
aaagagccta tcactcttcc attgtagaca ttttaaaata atgacactga ttttaacatt    7020
tttaagtgtc tttttagaac agagagcctg actagaacac agcccctcca aaaacccatg    7080
ctcaaattat ttttactatg gcagcaattc cacaaagggg aacaatgggt ttagaaatta    7140
caatgaagtc atcaacccaa aaaacatccc tatccctaag aaggttatga tataaaatgc    7200
ccacaagaaa tctatgtctg ctttaatctg tcttttattg ctttggaagg atggctatta    7260 cattttagt ttttgctgtg aatacctgag cagtttctct catccatact tatccttcac    7320
acatcagaag tcaggataga atatgaatca ttttaaaaac ttttacaact ccagagccat    7380
gtgcataaga agcattcaaa acttgccaaa acatacattt tttttcaaat ttaaagatac    7440 tctattttg tattcaatag ctcaacaact gtggtcccca ctgataaagt gaagtggaca    7500
aggagacaag taatggcata agtttgtttt tcccaaagta tgcctgttca atagccattg    7560
gatgtgggaa atttctacat ctcttaaaat tttacagaaa atacatagcc agatagtcta    7620
gcaaaagttc accaagtcct aaattgctta tccttacttc actaagtcat gaaatcattt    7680
taatgaaaag aacatcacct aggttttgtg gtttcttttt ttcttattca tggctgagtg    7740
aaaacaacaa tctctgtttc tccctagcat ctgtggacta tttaatgtac cattattcca    7800
cactctatgg tccttactaa atacaaaatt gaacaaaaag cagtaaaaca actgactctt    7860
cacccatatt ataaaatata atccaagcca gattagtcaa catccataag atgaatccaa    7920
gctgaactgg gcctagatta ttgagttcag gttggatcac atccctatttt attaataaac    7980 ttaggaaaga aggccttaca gaccatcagt tagctggagc taatagaacc tacacttcta    8040
aagttcggcc tagaatcaat gtggccttaa aagctgaaaa gaagcaggaa agaacagttt    8100
tcttcaataa tttgtccacc ctgtcactgg agaaaattta agaatttggg ggtgttggta    8160
gtaagttaaa cacagcagct gttcatggca gaaattattc aatacatacc ttctctgaat    8220
atcctataac caaagcaaag aaaaacacca aggggtttgt tctcctcctt ggagttgacc    8280
tcattccaag gcagagctca ggtcacaggc acagggctg cgcccaagct tgtccgcagc    8340
cttatgcagc tgtggagtct ggaagactgt tgcaggactg ctggcctagt cccagaatgt    8400
cagcctcatt ttcgatttac tggctcttgt tgctgtatgt catgctgacc ttattgttaa    8460
acacaggttt gtttgctttt tttccactca tggagacatg ggagaggcat tatttttaag    8520
ctggttgaaa gctttaaccg ataaagcatt tttagagaaa tgtgaatcag gcagctaaga    8580
aagcatactc tgtccattac ggtaaagaaa atgcacagat tattaactct gcagtgtggc    8640
attagtgtcc tggtcaatat tcggatagat atgaataaaa tatttaaatg gtattgtaaa    8700
```

```
tagttttcag gacatatgct atagcttatt tttattatct tttgaaattg ctcttaatac   8760
atcaaatcct gatgtattca atttatcaga tataaattat tctaaatgaa gcccagttaa   8820
atgttttgt cttgtcagtt atatgttaag tttctgatct cttgtctat gacgtttact    8880
aatctgcatt tttactgtta tgaattattt tagacagcag tggtttcaag cttttgcca   8940
ctaaaatac cttttatttt ctcctccccc agaaagtct ataccttgaa gtatctatcc   9000
accaaactgt acttctatta agaaatagtt attgtgtttt cttaatgttt tgttattcaa   9060
agacatatca atgaaagctg ctgagcagca tgaataacaa ttatatccac acagatttga   9120
tatatttgt gcagccttaa cttgatagta taaaatgtca ttgcttttta aataatagtt   9180
agtcaatgga cttctatcat agcttttccta aactaggtta agatccagag ctttggggtc   9240
ataatatatt acatacaatt aagttatctt tttctaaggg ctttaaaatt catgagaata   9300
accaaaaaag gtatgtggag agttaataca aacataccat attcttgttg aaacagagat   9360
gtggctctgc ttgttctcca taaggtagaa atactttcca gaatttgcct aaactagtaa   9420
gccctgaatt tgctatgatt agggatagga agagatttc acatggcaga ctttagaatt   9480
cttcactta gccagtaaag tatctccttt tgatcttagt attctgtgta ttttaacttt    9540
tctgagttgt gcatgtttat aagaaaaatc agcacaaagg gttaagtta aagccttttt    9600
actgaaattt gaaagaaaca gaagaaata tcaaagttct ttgtattttg agaggattaa    9660
atatgattta caaagttac atggagggct ctctaaaaca ttaaattaat tatttttgt    9720
tgaaagtct tactttagc atcattttat tcctcagcaa ctagctgtga agcctttact    9780
gtgctgtatg ccagtcactc tgctagattg tggagattac cagtgttccc gtcttctccg   9840
agcttagagt tggatgggga ataaagacag gtaaacagat agctacaata ttgtactgtg   9900
aatgcttatg ctggaggaag tacagggaac tattggagca cctaagagga gcacctacct   9960
tgaatttagg ggttagcaga ggcatcctga aaaagtcaa agctaagcca caatctataa  10020
gcagtttagg aattagcaga acgtgcgtgg tgaggagatg ccaaaggcaa gaagagaaga  10080
gtattccaaa caggagggat tccaaagaga gaagagtatc ccaaacaaca tttgcacaaa  10140
cctgatgggg agagagaatg tggggtgggg atggatgatg agactgaaga agaaagccag  10200
gtctagataa tcagtggcct tgtacaccat gttaaagagt gtagacttga ttctgttgta  10260
aacaggaaag cagcacaatt catatgaata ttttagaaga ctcccactgg aatatggaga  10320
ataaagttgg agatgactaa tcctggaagc agggagaaca ttttgagga agttgcacta  10380
ttttggtgaa aatgatgatc ataaacatga agaattgtag gtgatcatga cctcctctct  10440
aattttccag aagggttttg gaagatataa cataggaaca ttgacaggac tgacgaaagg  10500
agatgaaata caccatataa attgtcaaac acaaggccag atgtctaatt attttgctta  10560
tgtgttgaaa ttacaaattt ttcatcagga aaccaaaaac tacaaaactt agttttccca  10620
agtcccagaa ttctatctgt ccaaacaatc tgtaccactc cacctatatc cctacctttg  10680
catgtctgtc caacctcaaa gtccaggtct atacacacgg gtaagactag agcagttcaa  10740
gtttcagaaa atgagaaaga ggaactgagt tgtgctgaac ccatacaaaa taaacacatt  10800
ctttgtatag attcttggaa cctcgagagg aattcaccta actcataggt atttgatggt  10860
atgaatccat ggctgggctc ggcttttaaa aagccttatc tgggattcct tctatggaac  10920
caagttccat caaagcccat ttaaaagcct acattaaaaa caaaattctt gctgcattgt  10980
atacaaataa tgatgtcatg atcaaataat cagatgccat tatcagtggg aattacaaaa  11040
tggtatacccc actccaaaaa aaaaaaaaaa gctaaattct cagtagaaca ttgtgacttc  11100
```

-continued

```
atgagccctc cacagccttg gagctgagga gggagcactg gtgagcagta ggttgaagag    11160
aaaacttggc gcttaataat ctatccatgt tttttcatct aaaagagcct tcttttttgga   11220 ttaccttatt caatttccat caaggaaatt gttagttcca ctaaccagac agcagctggg    11280
aaggcagaag cttactgtat gtacatggta gctgtgggaa ggaggtttct ttctccaggt    11340
cctcactggc catacaccag tcccttgtta gttatgcctg tcatagacc cccgttgcta     11400 tcatctcata tttaagtctt tggcttgtga atttatctat tctttcagct tcagcactgc    11460
agagtgctgg gactttgcta acttccattt cttgctggct tagcacattc tcataggcc     11520 cagctctttt ctcatctggc cctgctgtgg agtcaccttg cccccttcagg agagccatgg   11580 cttaccactg cctgctaagc ctccactcag ctgccaccac actaaatcca agcttctcta    11640
agatgttgca gactttacag gcaagcataa aaggcttgat cttcctggac ttcccttttac   11700 ttgtctgaat ctcacctcct tcaactttca gtctcagaat gtaggcattt gtcctcttg     11760 ccctacatct tccttcttct gaatcatgaa agcctctcac ttcctcttgc tatgtgctgg    11820
aggcttctgt caggttttag aatgagttct catctagtcc tagtagcttt tgatgcttaa    11880
gtccaccttt taaggatacc tttgagattt agaccatgtt tttcgcttga gaagccta     11940 atctccagac ttgcctttct gtggatttca agaccaact gaggaagtca aaagctgaat     12000
gttgactttc tttgaacatt tccgctataa caattccaat tctcctcaga gcaatatgcc    12060
tgcctccaac tgaccaggag aaaggtccag tgccaaagag aaaaacacaa agattaatta   12120
tttcagttga gcacatactt tcaaagtggt ttgggtattc atatgaggtt ttctgtcaag    12180
agggtgagac tcttcatcta tccatgtgtg cctgacagtt ctcctggcac tggctggtaa    12240
cagatgcaaa actgtaaaaa ttaagtgatc atgtatttta acgatatcat cacatactta    12300
ttttctatgt aatgttttaa atttccccta acatactttg actgttttgc acatggtaga    12360
tattcacatt ttttgtgtt gaagttgatg caatcttcaa agttatctac cccgttgctt     12420
attagtaaaa ctagtgttaa tacttggcaa gagatgcagg gaatctttct catgactcac    12480
gccctattta gttattaatg ctactaccct attttgagta agtagtaggt ccctaagtac    12540
attgtccaga gttatacttt taaagatatt tagccccata tacttcttga atctaaagtc    12600
atacaccttg ctcctcattt ctgagtggga aagacatttg agagtatgtt gacaattgtt    12660
ctgaaggttt ttgccaagaa ggtgaaactg tcctttcatc tgtgtatgcc tggggctggg    12720
tccctggcag tgatggggtg acaatgcaaa gctgtaaaaa ctaggtgcta gtgggcacct    12780
aatatcatca tcatatactt attttcaagc taatatgcaa aatcccatct ctgtttttaa    12840
actaagtgta gatttcagag aaaatatttt gtggttcaca taagaaaaca gtctactcag    12900
cttgacaagt gttttatgtt aaattggctg gtggtttgaa atgaatcatc ttcacataat    12960
gttttcttta aaaatattgt gaatttaact ctaattcttg ttattctgtg tgataataaa    13020
gaataaacta atttcta                                                   13037
```

<210> SEQ ID NO 7
<211> LENGTH: 21
<212> TYPE: DNA
<213> ORGANISM: Artificial sequence
<220> FEATURE:
<223> OTHER INFORMATION: Artificial sequence = synthetic construct

<400> SEQUENCE: 7
gguguucgau gugaccaaat t                                              21

```
<210> SEQ ID NO 8
<211> LENGTH: 21
<212> TYPE: DNA
<213> ORGANISM: Artificial sequence
<220> FEATURE:
<223> OTHER INFORMATION: Artificial sequence = synthetic construct

<400> SEQUENCE: 8
uuuggucaca ucgaacacct t                                              21

<210> SEQ ID NO 9
<211> LENGTH: 21
<212> TYPE: DNA
<213> ORGANISM: Artificial sequence
<220> FEATURE:
<223> OTHER INFORMATION: Artificial sequence = synthetic construct

<400> SEQUENCE: 9
ggaagcacug aaggaugagt t                                              21

<210> SEQ ID NO 10
<211> LENGTH: 21
<212> TYPE: DNA
<213> ORGANISM: Artificial Sequence
<220> FEATURE:
<223> OTHER INFORMATION: Artificial sequence = synthetic construct

<400> SEQUENCE: 10
cucauccuuc agugcuucct t                                              21

<210> SEQ ID NO 11
<211> LENGTH: 21
<212> TYPE: DNA
<213> ORGANISM: Artificial sequence
<220> FEATURE:
<223> OTHER INFORMATION: Artificial sequence = synthetic construct

<400> SEQUENCE: 11
ggaucaacuu uuagucaugt t                                              21

<210> SEQ ID NO 12
<211> LENGTH: 21
<212> TYPE: DNA
<213> ORGANISM: Artificial sequence
<220> FEATURE:
<223> OTHER INFORMATION: Artificial sequence = synthetic construct

<400> SEQUENCE: 12
caugacuaaa aguugaucct t                                              21

<210> SEQ ID NO 13
<211> LENGTH: 20
<212> TYPE: DNA
<213> ORGANISM: Artificial sequence
<220> FEATURE:
<223> OTHER INFORMATION: Artificial sequence = synthetic construct

<400> SEQUENCE: 13
catggtcctt ggaggtcgaa                                                20

<210> SEQ ID NO 14
<211> LENGTH: 21
<212> TYPE: DNA
<213> ORGANISM: Artificial sequence
<220> FEATURE:
<223> OTHER INFORMATION: Artificial sequence = synthetic construct

<400> SEQUENCE: 14
```
gagagcaaca gcatccagtg c                                              21

<210> SEQ ID NO 15
<211> LENGTH: 19
<212> TYPE: DNA
<213> ORGANISM: Artificial sequence
<220> FEATURE:
<223> OTHER INFORMATION: Artificial sequence = synthetic construct

<400> SEQUENCE: 15
caacggcaag gtgttcgat                                                 19

<210> SEQ ID NO 16
<211> LENGTH: 20
<212> TYPE: DNA
<213> ORGANISM: Artificial sequence
<220> FEATURE:
<223> OTHER INFORMATION: Artificial sequence = synthetic construct

<400> SEQUENCE: 16
tccagcaaag accccatacg                                                20

<210> SEQ ID NO 17
<211> LENGTH: 20
<212> TYPE: DNA
<213> ORGANISM: Artificial sequence
<220> FEATURE:
<223> OTHER INFORMATION: Artificial sequence = synthetic construct

<400> SEQUENCE: 17
gtgcaaggtt ggagacagct                                                20

<210> SEQ ID NO 18
<211> LENGTH: 20
<212> TYPE: DNA
<213> ORGANISM: Artificial sequence
<220> FEATURE:
<223> OTHER INFORMATION: Artificial sequence = synthetic construct

<400> SEQUENCE: 18
tttgcccttc agaagcggac                                                20

<210> SEQ ID NO 19
<211> LENGTH: 18
<212> TYPE: DNA
<213> ORGANISM: Artificial sequence
<220> FEATURE:
<223> OTHER INFORMATION: Artificial sequence = synthetic construct

<400> SEQUENCE: 19
gaggatgtgg tggcgact                                                  18

<210> SEQ ID NO 20
<211> LENGTH: 20
<212> TYPE: DNA
<213> ORGANISM: Artificial sequence
<220> FEATURE:
<223> OTHER INFORMATION: Artificial sequence = synthetic construct

<400> SEQUENCE: 20
taatcatttt tccgggcact                                                20

REGULATORS OF THE NON-GENOMIC ACTION OF PROGESTERONE AND METHODS OF USE

CLAIM OF PRIORITY AND CROSS-REFERENCE TO RELATED APPLICATIONS

This application is a continuation-in-part of and claims priority to U.S. Ser. No. 11/732,780, filed Apr. 4, 2007, which claims priority to U.S. Provisional Patent Application Ser. No. 60/789,301, filed Apr. 5, 2006, both of which are herein incorporated by reference in their entireties.

STATEMENT OF GOVERNMENT SUPPORT

This invention was made with government funding under Grant # HD 34383 from the National Institutes of Health. The government has certain rights in the invention.

FIELD

This application relates to regulators of the non-genomic action of progesterone and use of the regulators for treating progesterone related diseases, such as ovarian cancer. The application more specifically relates to pharmaceutical compositions and methods for inducing progesterone regulated apoptosis and methods of diagnosis, staging, and/or prognosis of ovarian cancer.

BACKGROUND

Ovarian cancer kills more women than all the other gynecologic cancers combined and is the fourth leading cause of cancer death among women in the United States. In fact, one in 57 women will be ultimately diagnosed with ovarian cancer. When this cancer is detected early, the five-year survival rate is greater than 90%. However, only 24% of the cancers are detected early. As a result most ovarian cancers are detected in more advanced stages in which the cancer cells have spread outside the ovary. Once the ovarian cancer has spread, the five-year survival rate decreases to less than 25%.

Treatment of patients with ovarian cancer consists of surgery to remove the ovary, the uterus and the tumor. This is usually followed by platinum-based (carboplatin and cisplatin) chemotherapy. In spite of these intense surgical and chemotherapeutic treatments, the ovarian cancer more often than not recurs. At this point the patients are given salvage chemotherapy and possibly de-bulking surgery to remove the tumors that are usually distributed throughout the peritoneum. Again platinum-based chemotherapy is often used to treat the recurrent ovarian cancers but many of the ovarian cancer cells are resistant to these platinum-based agents, and thus these drugs are relatively ineffective. Increasing the dosage of platinum-based drugs is not an effective approach because these drugs are very toxic.

The overall effectiveness of any regimen for advanced ovarian cancer containing a non-platinum based drug has not yet been established. The inability of the initial chemotherapy to effectively destroy the ovarian cancer results in its recurrence and ultimately the loss of life. Progesterone (also known as 4-Pregnene-3,20-dione or P4) is a steroid hormone secreted by the ovary. Progesterone influences the function of numerous mammalian organ systems including regulation of the function of the hypothalamus, pituitary, ovary, uterus and mammary gland.

Progesterone also affects the various pathological states of these tissues including endometriosis and cancers of the ovary and breast. Depending on the ovarian cell type, progesterone can be either apoptotic (inducing cell death and thereby inhibiting cell growth) or anti-apoptotic (promoting cell growth). It has been observed that progesterone protects against ovarian cancer.

Progesterone regulates the function of the normal and neoplastic mammalian ovary through genomic (or nuclear) and non-genomic (or membrane-initiated) mechanisms. In the genomic mechanism, progesterone binds and activates progesterone receptors (PGR), namely progesterone receptors A and B (PGR-A and PGR-B), which translocate to the nucleus of the cell where they function as transcription factors, inducing the expression of numerous specific genes. In the non-genomic mechanism, progesterone also evokes rapid responses by binding to membrane receptors, including Progesterone Receptor Membrane Component-1 (PGRMC1), which was initially identified as a membrane progesterone binding protein in liver. PGRMC1 forms a progesterone receptor complex with Plasminogen Activator Inhibitor mRNA Binding Protein-1 (PAIRBP1).

The genomic mechanism of progesterone is independent from its non-genomic mechanism. It is generally believed that the protective action of progesterone against ovarian cancer is achieved through PGR in the genomic mechanism. However, it has also been recognized that PGR is expressed within the ovary in a cell specific and hormonally regulated manner. One of the major pharmaceutical agents developed on the basis of PGR's genomic actions is RU486. However, the effectiveness of this pharmaceutical agent in the treatment of ovarian cancer is questionable.

Therefore, there is a great need for pharmaceutical compositions and methods to improve the effectiveness of chemotherapy to treat ovarian cancer by regulating the action of progesterone.

SUMMARY

Compositions containing regulators of the non-genomic actions of progesterone, and methods of use are provided herein. In particular, the progesterone regulators act through a previously unrecognized progesterone receptor complex that is located on the plasma membrane. Also provided are compositions and methods of using regulators to inhibit progesterone non-genomic actions, such as for the treatment of diseases involving progesterone-responsive tissues.

The progesterone regulators are useful for improving the effectiveness of chemotherapy for the treatment of progesterone-related cancers, particularly for cancers of the ovary, uterus or breast. The progesterone regulators are also useful as agents for the diagnosis and prognosis of progesterone-responsive diseases. When used for pharmaceutical administration, the compositions described herein contain the progesterone regulator in a pharmaceutically acceptable carrier.

The progesterone regulator achieves the desired inhibition of progesterone non-genomic action by impeding the binding of progesterone to a progesterone receptor complex on a progesterone-responsive diseased tissue such as a tumor or diseased endometrial tissue. Progesterone binding is impeded by blocking the binding of progesterone to the progesterone receptor complex, by reducing the amount of one or more proteins that make up the receptor complex or by inhibiting the interactions of molecules to form the receptor complex. In one embodiment, the progesterone regulator binds to the progesterone receptor complex to block the binding of progesterone to the receptor. In another embodiment, the progesterone regulator reduces the production of PGRMC1, PAIRBP1, or both. In yet another embodiment, the progesterone regulator interferes with the interaction between PGRMC1 and PAIRBP1 to inhibit formation of the receptor complex. The inhibitory effect may be accomplished by depleting or blocking the extracellular domain of PGRMC1.

Suitable progesterone regulators include, but are not limited to, peptides and nucleic acid molecules. Preferably, the progesterone regulator is a chemical compound, a peptide, a DNA molecule encoding a peptide, a nucleic acid molecule such as a small interfering RNA (siRNA), a protein, or an antibody. Suitable progesterone regulators may be based on the discovery of critical sequences in PGRMC1 required for interaction with PAIRBP1 and/or required for interaction with progesterone. For example, the first 20 amino acids of PGRMC1 make up the extracellular domain of this protein and have the amino acid sequence of SEQ ID NO:1 or SEQ ID NO:2. Useful progesterone regulators include peptides or DNA molecules encoding peptides having an amino acid sequence with at least about 60%, 80% or 90% homology to the extracellular domain of PGRMC1. Suitable progesterone regulators also include antibodies that bind to the extracellular domain of PGRMC1.

In one embodiment, the progesterone regulator is a peptide and the composition may optionally contain an additional peptide that directs the progesterone regulator to the cancer, such as luteinizing hormone. This additional peptide may be coupled to the progesterone regulator, using methods well known to those skilled in the art, such as in a fusion protein. In addition, the progesterone regulator may optionally be provided in combination with a pharmaceutical agent, such as an anti-cancer drug, to facilitate the agents' specificity for diseased cells that express the progesterone receptor complex.

Treatment of a disease involving progesterone-responsive tissue is achieved by administering one or more of the progesterone regulator compositions described herein. Diseases involving a progesterone-responsive tissue to be treated include endometriosis and cancers, such as but not limited to, cancers of the ovary, uterus or breast.

Also provided herein are methods for the detection of abnormal functionality involved in progesterone's non-genomic actions, which are useful for diagnosing patients having pathological conditions that are likely to respond to chemotherapy and for providing prognostic information.

Also provided herein are methods for diagnosing, prognosing, and staging ovarian cancers.

Accordingly, it is an object of the present invention to provide a progesterone regulator of the non-genomic actions of progesterone.

It is another object of the present invention to provide a progesterone regulator that selectively inhibits the interaction between PGRMC1 and PAIRBP1 on the plasma membrane without influencing nuclear progesterone receptors.

It is another object of the present invention to provide a progesterone regulator that inhibits progesterone's anti-apoptotic effect by targeting PGRMC1.

It is another object of the present invention to identify the specific sites or domains of PGRMC1 that interact with PAIRBP1.

It is yet another object of the present invention to provide a pharmaceutically acceptable composition containing a progesterone regulator.

It is yet another object of the present invention to provide a method of treating diseases involving a progesterone-responsive tissue by administering a pharmaceutically acceptable composition containing a progesterone regulator.

It is yet another object of the present invention to provide a method of treating cancer in which the effectiveness of an anti-cancer chemotherapy is improved by administering a pharmaceutically acceptable composition containing a progesterone regulator and an anti-cancer drug.

These and other objects, features and advantages of the present invention will become apparent after a review of the following detailed description of the disclosed embodiments and the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
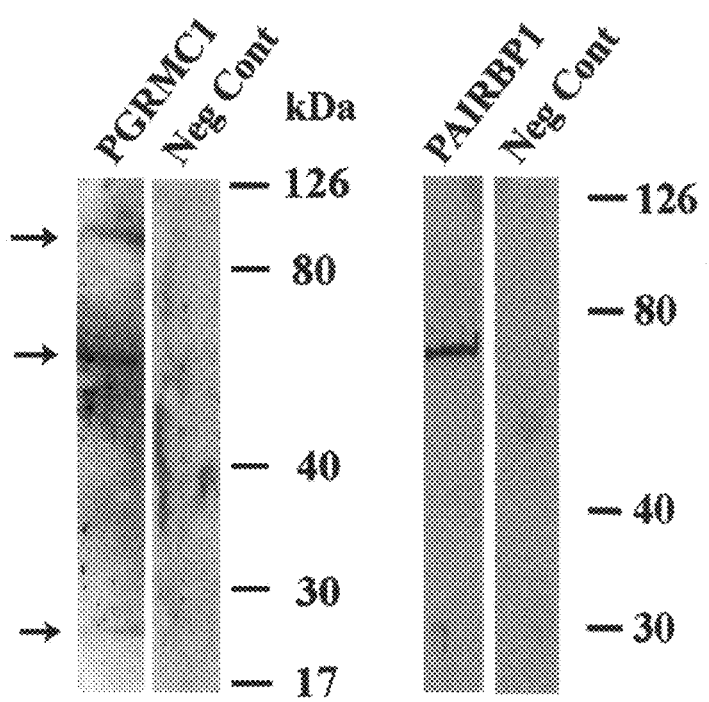
FIG. 1 is a scan of a western blot showing expression of Progesterone Receptor Membrane Component-1 (PGRMC1; left panel) and its binding partner, Plasminogen Activator Inhibitor mRNA Binding Protein-1 (PAIRBP1; right panel), in human granulosa/luteal cells. Note that although PGRMC1 is approximately 28 kDa, it often is detected as a 56 kDa dimer or as an oligomer. These different molecular weight forms of PGRMC1 are indicated by an arrow on the left panel.

Progesterone regulators, or agents, having the ability to modulate or inhibit progesterone non-genomic action are provided. The progesterone regulators described herein inhibit the anti-apoptotic effects of progesterone and are useful for the treatment of diseases involving progesterone-responsive tissues. The progesterone regulators are also useful for improving the effectiveness of chemotherapy used to treat progesterone-related cancers, particularly for cancers of the ovary, uterus or breast. In addition, the progesterone regulators are useful as agents for the diagnosis and prognosis of progesterone-responsive diseases. The attenuation of progesterone's anti-apoptotic action may be achieved by either impairing the binding of progesterone to its membrane receptor or by disrupting the interaction between PGRMC1 and PAIRBP1 on progesterone-responsive disease tissues. This attenuates the anti-apoptotic effects of progesterone and provides a unique method for treating progesterone-supported cell growth and reducing the resistance of cancer cells, including breast and ovarian cancer cells, to chemotherapy.

Compositions

Compositions are provided that contain the progesterone regulator described herein in a pharmaceutically acceptable carrier. As explained above, the progesterone regulator modulates or inhibits progesterone non-genomic action. The progesterone regulator achieves this effect by impeding the function of a progesterone receptor complex on a progesterone-responsive diseased tissue such as a tumor or diseased endometrial tissue. This is achieved by either blocking the binding of progesterone to the receptor complex or by reducing the amount of one or more proteins that form the receptor complex. In one embodiment, the progesterone regulator binds to the progesterone receptor complex in such a way that it directly blocks or impedes the binding of progesterone to the receptor. In another embodiment, the progesterone regulator reduces the production of either PGRMC1, PAIRBP1, or both, thereby inhibiting the formation of the progesterone receptor complex. In yet another embodiment, the progesterone regulator interferes with the interaction between PGRMC1 and PAIRBP1, thereby inhibiting the ability of these molecules to form a functional progesterone receptor complex.

Chemotherapeutic agents such as cisplatin (also known as cis-diamminedichloroplatinum(II)) kill ovarian cancer cells by inducing death by apoptosis. However, cisplatin fails to kill 100% of the cancer cells and, inadvertently, induces apoptosis in normal cells, causing poor therapeutic results, and adverse side effects. Normally, PGRMC1 interacts with PAIRBP1 to form the progesterone receptor complex. Progesterone binds to this progesterone receptor complex and activates intracellular survival pathways that prevent apoptosis. Because some cells, such as ovarian cancer cells, synthesize progesterone, ovarian cancer cells establish conditions that promote their own survival, making them more resistant to chemotherapeutic agents such as cisplatin. It has been discovered that the progesterone produced by these cancer cells counteracts the apoptotic effects of cisplatin, thereby allowing the cancer cells to thrive.

It will be appreciated that the terms "progesterone regulator" and "progesterone agent" as used herein are interchangeable and are defined herein as any chemical compound or biological molecule capable of selectively regulating the action of progesterone through a non-genomic mechanism without affecting progesterone's genomic mechanism. Suitable biological molecules having the desired non-genomic inhibitory effect include, but are not limited to, peptides and nucleic acid molecules. "Progesterone non-genomic action" is defined herein as non-nuclear action or action through a mechanism other than via PGR. For example, progesterone non-genomic action may occur by way of a membrane receptor in a progesterone-responsive tissue.

Preferably, the progesterone regulator is a chemical compound, a peptide, a DNA molecule encoding a peptide, a nucleic acid molecule such as a small interfering RNA (siRNA), a protein, or an antibody. In one embodiment, the progesterone regulator impedes or blocks the binding of progesterone to the progesterone receptor complex, preferably by the binding of the progesterone regulator, most likely compose of a peptide or protein, to the progesterone receptor complex. In another embodiment, the progesterone regulator acts by depleting the expression of PGRMC1 or PAIRBP1. The reduced production of either or both of these proteins results in a reduction in the amount of functional progesterone receptor complex available for binding to progesterone. In another embodiment, the progesterone regulator inhibits the interaction or binding between PGRMC1 and PAIRBP1 to form the progesterone receptor complex. In the absence of this complex, progesterone fails to bind to cells of the diseased tissue, and progesterone's ability to block apoptosis is impeded. In this way, the progesterone regulator causes cells of the diseased tissue to become more susceptible to chemotherapies relying on apoptosis, such as platinum-based chemotherapies, particularly cisplatin. Accordingly, blockage of the progesterone binding site on the progesterone receptor complex, reduced expression of the molecules that interact to form the progesterone receptor complex, and disruption of the interaction between PGRMC1 and PAIRBP1 may lead to the complete attenuation of progesterone's ability to inhibit apoptosis.

Figure 7A:
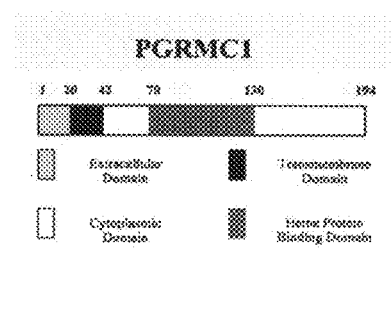
FIG. 7A is a schematic representation of the structural organization of progesterone receptor membrane component-1 (PGRMC1). The numbers above each structure refer to the amino acid number. A series of deletion mutants were constructed and named according to the amino acids that they encode (i.e., 1-194 encodes the entire PGRMC1 molecule).
Figure 7B:
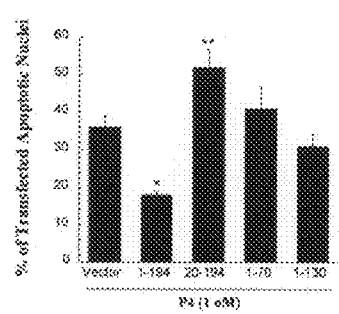
FIG. 7B is a bar graph showing percent transfected cells with apoptotic nuclei. These mutants were transfected into SIGC cells, and SIGC cells that expressed each of these mutants were monitored by their ability to undergo apoptosis.
Figure 7C:
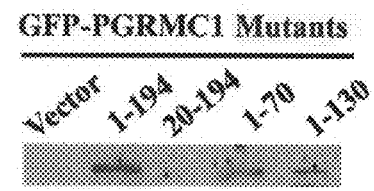
FIG. 7C is a reproduction of a western blot showing the ability of each of these constructs to bind to PAIRBP1. In this assay, each mutant was isolated using GFP affinity beads, and the ability of the mutant to bind PAIRBP1 was assessed.

Suitable progesterone regulators may be based on the discovery of critical sequences in PGRMC1 required for interaction with PAIRBP1 and/or required for interaction with progesterone. A series of GFP-PGRMC1 mutants were generated to identify the amino acid sequence within PGRMC1 that interacts with PAIRBP1 (FIGS. 7B and 7C). The numbers associated with each mutant denote the amino acids they encode. While the wild-type (1-194) transduces progesterone's action, the deletion of any section results in an inability to mediate progesterone's action. This suggests that there are different functional domains throughout PGRMC1. The first 20 amino acids of PGRMC1 make up the extracellular domain of this protein. Depletion of the first 20 amino acids of PGRMC1, leads to a rate of apoptosis that is even greater than the vector alone or other mutants. Furthermore, the extracellular domain (FIG. 7A) of PGRMC1, is required for its interaction with PAIRBP1. Based on a BLAST search, the sequence of the first 20 amino acids of PGRMC1 is unique and appears to occur only in the PGRMC1 protein.

The first 20 amino acids of PGRMC1 have the amino acid sequence MAAEDVVATGADPSELELLL (SEQ ID NO:1). In an alternative embodiment, the first 20 amino acids of PGRMC1 have the amino acid sequence MAAEDVVAT-GADPSDLESGG (SEQ ID NO:2).

Useful progesterone regulators inhibit or prevent the binding between PGRMC1 and PAIRBP1 or the expression of one or more of these molecules. Suitable progesterone regulators include PGRMC1 specific siRNA molecules capable of depleting PGRMC1 in progesterone-supported cancer cells. Useful progesterone regulators also include agents, such as chemical compounds or biological molecules, that are capable of blocking progesterone from binding specifically to cancer cells, such as antibodies against either PGRMC1 or PAIRBP1. Other regulators include peptides or DNA molecules encoding peptides having an amino acid sequence with at least about 60%, 70%, 80% or 90% homology with the extracellular domain (i.e. the first 20 amino acids) of PGRMC1. These peptides are useful as progesterone regulators because they may compete with PGRMC1 for the ability to interact with PAIRBP1. Preferably, the progesterone regulator is a peptide or DNA encoding a peptide having an amino acid sequence with at least about 60%, 70%, 80% or 90% homology to the first 20 amino acids of PGRMC1, set forth above as SEQ ID NO:1 or, alternatively, SEQ ID NO:2.

Alternatively, the progesterone regulator is an antibody that binds to the extracellular domain of PGRMC1 to block or impair the ability of PGRMC1 to interact with PAIRBP1 to form the progesterone receptor complex. Preferably, the progesterone regulator is an antibody that binds to the first 20 amino acids of PGRMC1. More preferably, the progesterone regulator is an antibody that binds to the domain of PGRMC1 having the amino acid sequence of SEQ ID NO:1 or 2.

Although not wishing to be bound by the following, it is believed that disruption of the receptor complex of PGRMC1 and PAIRBP1 in ovarian cancer cells decreases the progesterone-supported viability of the cancer cells. PGRMC1 and its binding partner, PAIRBP1, are potential targets that could block progesterone's anti-apoptotic action, thereby reducing the viability of cancer cells and improving the effectiveness of chemotherapy.

When the progesterone regulator is a peptide, the composition may optionally contain an additional peptide sequence that includes all or part of a sequence encoding a peptide that directs the progesterone regulator to the diseased tissue or cancer, particularly a progesterone-related cancer. For example, the receptor for the luteinizing hormone (LH) is highly expressed in ovarian and breast cancers. Therefore, a fusion protein composed of the progesterone regulator coupled to LH is useful for more selectively delivering the progesterone agent to the ovarian or breast cancer cells.

In addition, the progesterone regulator (such as a peptide or siRNA) may optionally be provided in combination with and/or covalently linked to a chemotherapeutic agent, or an anti-cancer drug, to facilitate the agents' specificity for cancer cells that express the progesterone receptor complex. In this way, the progesterone regulator functions as an adjunct treatment. Chemotherapeutic agents useful in combination with the progesterone regulator include those administered for the treatment of progesterone-related cancers such as, but not limited to, platinum-based agents such as carboplatin and cisplatin.

Ideally, the composition is a pharmaceutical composition containing the progesterone regulator described herein in combination with a pharmaceutically acceptable carrier for administration to a mammal, such as a human patient, as described in more detail below.

Methods of Treatment

Treatment of a disease involving a progesterone-responsive tissue is achieved by administering the pharmaceutical composition provided herein, which contains a progesterone regulator capable of attenuating a non-genomic action of progesterone. Suitable compositions and progesterone regulators are described herein.

Diseases involving a progesterone-responsive tissue to be treated include endometriosis and cancers, such as but not limited to, cancers of the ovary, uterus or breast.

An ovarian cancer patient may be treated conventionally with surgery, radiation or chemotherapy, and then a pharmaceutical composition containing a progesterone agent is subsequently administered to the patient to reduce progesterone-supported resistance of the cancer cells.

The progesterone regulators described herein can be provided as substantially purified compositions and placed in pharmaceutically acceptable formulations using formulation methods known to those of ordinary skill in the art. These formulations can be administered by standard routes. In general, the compositions may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the progesterone regulator may be incorporated into biodegradable polymers allowing for sustained release, the polymers being implanted in the vicinity of where drug delivery is desired, for example, at the site of a tumor or implanted for systemic slow release. Osmotic minipumps may also be used to provide controlled delivery of high concentrations of the progesterone regulator, through cannulae to the site of interest, such as directly into a metastatic growth or into the vascular supply to that tumor.

The effective dosage of the progesterone regulator provided herein will depend on the disease state or condition being treated and other clinical factors such as weight and condition of the human or animal and the route of administration of the agent. Depending upon the half-life of the agent in the particular animal or human, it can be administered between several times per day to once a week. It is to be understood that the methods provided herein have applications for both human and veterinary use. The methods described herein contemplate single as well as multiple administrations, given either simultaneously or over an extended period of time.

The progesterone agent formulations provided herein include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The progesterone agent formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions, which may contain anti-oxidants, buffers, bacteriostats and solutes that render the formulation isotonic with the blood of the intended recipient; and aqueous and non-aqueous sterile suspensions, which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the pharmaceutical composition may include other agents conventional in the art having regard to the type of formulation in question.

Methods of Diagnosis

Early diagnosis and treatment of cancer is known to enhance survival. Methods for the detection of abnormal functionality involved in progesterone's non-genomic actions are useful for diagnosing patients having pathological conditions that are likely to respond to chemotherapy and for providing prognostic information. The abnormal functionalities include PGRMC1's lack of an extracellular domain, progesterone's failure to bind specifically to PGRMC1, PGRMC1's failure to interact with PAIRBP1, and PGRMC1's failure to attenuate progesterone's anti-apoptotic activity. Suitable pathological conditions for diagnosis include diseases such as endometriosis and cancers involving progesterone-responsive tissues. The diagnostic methods include but not limited to the following techniques: competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, immunocytochemistry, immunohistochemistry, PCR, quantitative PCR, real-time PCR, quantitative real-time PCR, in situ PCR of tissue or cell samples, and the like. The skilled artisan will understand that any antibody-based, nucleic acid-based, mass spectroscopy-based, FRET-based, or similar technique for detecting PGRMC1 levels or PGRMC1/PGR ratios can be used in the diagnostic methods described herein.

Figure 5:
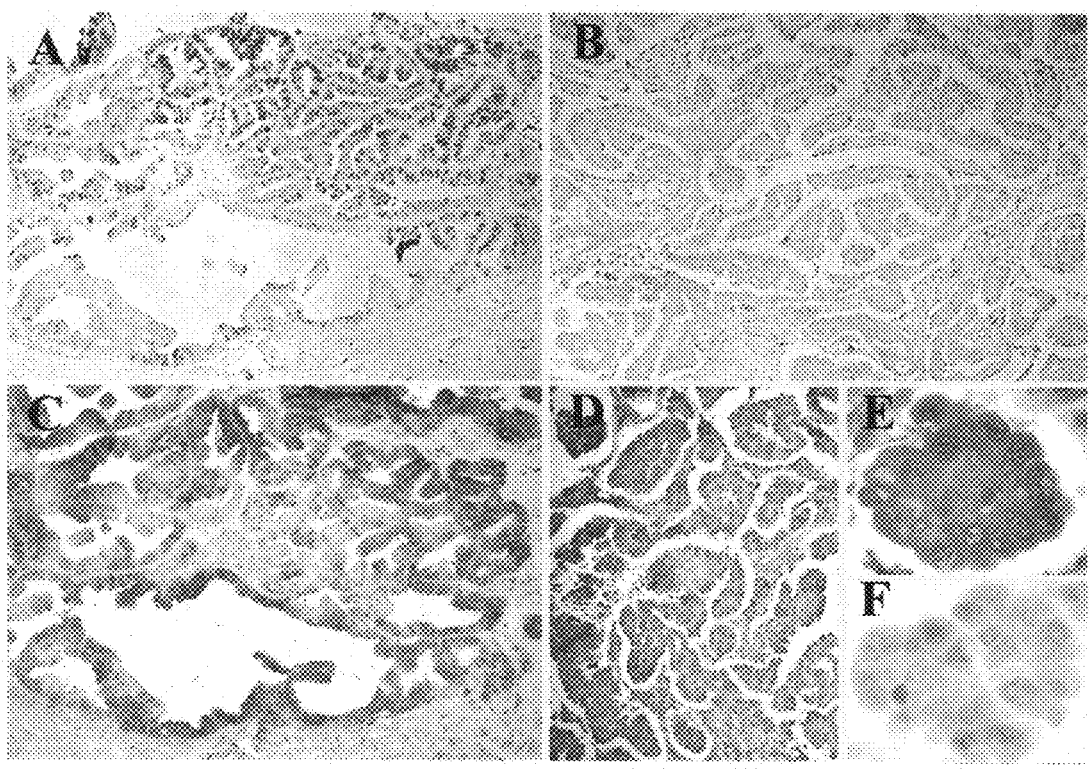
FIG. 5 is a collection of micrographs showing expression of PGR (panels A and B) and PGRMC1 (panels C, D and E) in Stage IIIb (panel A and panel C) and Stage IIIc (panel B, panel D and panel E) ovarian cancers. Each protein is revealed by a brown stain. Panel F is a negative control.

PGRMC1 is expressed in human ovarian cancer cells, including human ovarian cancer cell line Ovcar-3 and ovarian epithelial cell line referred to as spontaneously immortalized granulosa cells (SIGCs), as well as many tumors from patients having Stage I to IV serious ovarian cancers, in which PGR is not expressed. Even in the PGR positive tumors, very few areas within the entire tumor are positive for PGR. In contrast, as shown in the examples below, ovarian cancers express PGRMC1 regardless of whether or not they express PGR (FIG. 5). Moreover, PGRMC1 is detected in virtually 100% of the tumor cells in these tumors. This inverse relationship between PGR and PGRMC1 expression is supported by the observation that the expression of PGRMC1 is greater in PGR knockout mice than their wild-type controls. Interestingly, progesterone prevents the formation of ovarian tumors but does not affect their development once established. This is consistent with the observation that early stage tumors express PGR but that as they develop PGR expression is lost and only PGRMC1 is expressed. Therefore, PGRMC1 plays an important role in ovarian cancer development.

Detection of a disrupted interaction between PGRMC1 and PAIRBP1 or a disrupted progesterone binding to PGRMC1 is useful for identifying and diagnosing cancers that are likely to be responsive to chemotherapy. The detection may be performed using methods known to those skilled in the art such as by the use of a labeled antibody. For example, a monoclonal antibody may be generated against a peptide of SEQ ID NO:1 or SEQ ID NO:2. An ovarian tumor tissue sample may be obtained from a patient and incubated with the antibody. The bound antibody is then detected quantitatively using conventional detection methods for the presence of the extracellular domain of PGRMC1. The absence of the extracellular domain from PGRMC1 disrupts progesterone's non-genomic action such as progesterone-supported resistance of cancer cells to chemotherapy.

In addition, an application of FRET analysis may provide additional information as to whether the PGRMC1 interacts with PAIRBP1. Further, an analysis of potential mutations in PGRMC1 or PAIRBP1 gene in an ovarian tissue sample using conventional methods can also be carried out. Lack of the interaction between PGRMC1 and PAIRBP1 or progesterone specific binding to PGRMC1 in a tumor tissue from a patient provides valuable information as to whether the patient is likely to respond to chemotherapy.

The diagnostic and prognostic methods provided herein also include a detection of PGRMC1's down regulation of progesterone's anti-apoptotic effect (i.e., progesterone's inhibition of programmed cell death). To determine whether PGRMC1 regulates progesterone's biological actions such as its anti-apoptotic effect through the non-genomic mechanism in tumor cells, siRNAs for PGRMC1 and/or PAIRBP1 may be introduced into the ovarian cancer cells to deplete the expression of PGRMC1 and/or PAIRBP1. The effect of changing the expression levels of these proteins on progesterone's ability to inhibit apoptosis may then be monitored. Detection of an increasing percentage of apoptotic tumor cells from a patient upon depletion suggests that the patient is likely to respond to chemotherapy.

Provided herein is a method for detecting an ovarian carcinoma in an individual, comprising testing a sample from the individual for a level of PGRMC1 relative to a level of PGRMC1 found in a control sample from an individual with an ovarian carcinoma, whereby a level of PGRMC1 about equal to or greater than the level of PGRMC1 in the control sample detects an ovarian carcinoma in the individual.

Also provided herein is a method for detecting an ovarian carcinoma in an individual, comprising testing a sample from the individual for an increased ratio of PGRMC1/PGR relative to a ratio of PGRMC1/PGR found in a control sample from an individual lacking an ovarian carcinoma, whereby the increased ratio of PGRMC1/PGR detects an ovarian carcinoma in the individual.

Also provided herein is a method for identifying a stage 3 or stage 4 ovarian carcinoma in an individual, comprising testing a sample from the individual for an increased level of PGRMC1 relative to a level of PGRMC1 in a control sample from an individual having a stage 1 or stage 2 ovarian carcinoma, whereby the increased level of PGRMC1 identifies a stage 3 or stage 4 ovarian carcinoma in the individual.

Also provided herein is a method for identifying a stage 3 or stage 4 ovarian carcinoma in an individual, comprising testing a sample from the individual for a level of PGRMC1 relative to a level of PGRMC1 in a control sample from an individual having a stage 3 or stage 4 ovarian carcinoma, whereby a level of PGRMC1 that is about equal to or greater than the level in the control sample identifies a stage 3 or stage 4 ovarian carcinoma in the individual.

Also provided herein is a method for identifying a stage 3 or stage 4 ovarian carcinoma in an individual, comprising testing a sample from the individual for an increased ratio of PGRMC1/PGR relative to a ratio of PGRMC1/PGR in a sample from an individual having a stage 1 or stage 2 ovarian carcinoma, whereby the increased ratio of PGRMC1/PGR detects a stage 3 or stage 4 ovarian carcinoma in the individual.

Also provided herein is a method for identifying a stage 3 or stage 4 ovarian carcinoma in an individual, comprising testing a sample from the individual for a ratio of PGRMC1/PGR relative to a ratio of PGRMC1/PGR in a control sample from an individual having a stage 3 or stage 4 ovarian carcinoma, whereby a ratio of PGRMC1/PGR that is about equal to or greater than the level in the control sample detects a stage 3 or stage 4 ovarian carcinoma in the individual.

Also provided herein is a method of identifying an ovarian carcinoma that is at least partially resistant to platinum-based chemotherapy in an individual, comprising testing a sample from the individual for an increased level of PGRMC1 relative to a level of PGRMC1 in a control sample from an individual having an ovarian carcinoma that responds to platinum-based chemotherapy, whereby the increased level of PGRMC1 identifies an ovarian carcinoma that is at least partially resistant to platinum-based chemotherapy.

In the above method, detection of a level of PGRMC1 that is not increased relative to the control sample indicates an ovarian cancer that is sensitive to platinum-based chemotherapy.

Also provided is a method of identifying an ovarian carcinoma that is at least partially resistant to platinum-based chemotherapy in an individual, comprising testing a sample from the individual for a level of PGRMC1 relative to a level of PGRMC1 in a control sample from an individual having an ovarian carcinoma that is resistant to platinum-based chemotherapy, whereby a level of PGRMC1 that is about equal to or greater than the level in the control sample identifies an ovarian carcinoma that is at least partially resistant to platinum-based chemotherapy.

Also provided is a method for identifying an ovarian carcinoma that is at least partially resistant to platinum-based chemotherapy in an individual, comprising testing a sample from the individual for an increased ratio of PGRMC1/PGR relative to a ratio of PGRMC1/PGR in a control sample from an individual having an ovarian carcinoma that responds to platinum-based chemotherapy, whereby the increased ratio of PGRMC1/PGR identifies an ovarian carcinoma that is at least partially resistant to platinum-based chemotherapy.

In the above method, detection of a ratio of PGRMC1/PGR that is not about equal to or greater than that of the control sample indicates an ovarian cancer that is sensitive to platinum-based chemotherapy.

Also provided is a method for identifying an ovarian carcinoma that is at least partially resistant to platinum-based chemotherapy in an individual, comprising testing a sample from the individual for a ratio of PGRMC1/PGR relative to a ratio of PGRMC1/PGR in a control sample from an individual having an ovarian carcinoma that is resistant to platinum-based chemotherapy, whereby a ratio of PGRMC1/PGR that is about equal to or greater than the ratio in the control sample identifies an ovarian carcinoma that is at least partially resistant to platinum-based chemotherapy.

Any of the methods provided herein can further comprise recording the level of PGRMC1 or the ratio of PGRMC1/PGR detected in the sample. Recording can be, e.g., but not limited to: by electronic means, e.g., but not limited to, by electronically storing the result of an assay (e.g., on the hard drive of a computer, on a compact disc, on the internet, or by other electronic means), by recording the result on paper, or by reporting the result to an individual (e.g., a health care profession or the individual from whom a sample was obtained).

In any of the methods provided herein, the sample can be, e.g., but not limited to, a tumor sample, a tissue section, cells, blood, urine, sputum, nucleic acid, or protein.

In any of the methods provided herein, the level of PGRMC1 (or the ratio of PGRMC1/PGR) can be detected by detecting the level of PGRMC1 mRNA (or the ratio of PGRMC1/PGR mRNA) in the sample.

In any of the methods provided herein, the level of PGRMC1 (or the ratio of PGRMC1/PGR) can be detected by detecting the level of PGRMC1 protein (or the ratio of PGRMC1/PGR protein) in the sample.

Nucleic Acid and Polypeptide Sequences

Nucleic acid primers, probes, siRNAS, and antibodies for use in the methods described herein can be generated using techniques that are well known in the art. Polypeptide and nucleic acid sequences for PGRMC1 and PGR are well known in the art and can be obtained from publicly available sources, for example, polypeptide and nucleic acid sequence databases available through the National Center for Biotechnology Information (NCBI).

An example of a polypeptide sequence for human PGRMC1 is GenBank Accession No. CAG33274:

```
                                            (SEQ ID NO: 3)
MAAEDVVATGADPSDLESGGLLHEIFTSPLNLLLLGLCIFLLYKIVRGDQ

PAASGDSDDEPPPLPRLKRRDFTPAELRRFDGVQDPRILMAINGKVFDV

TKGRKFYGPEGPYGVFAGRDASRGLATFCLDKEALKDEYDDLSDLTAAQQ

ETLSDWESQFTFKYHHVGKLLKEGEEPTVYSDEEEPKDESARKND.
```

An example of a nucleotide sequence for human PGRMC1 is GenBank Accession No. CR456993 (stop codon "taa" is indicated): atggctgccg aggatgtggt ggcgactggc gccgacccaa

```
                                            (SEQ ID NO: 4)
   atggctgccg aggatgtggt ggcgactggc gccgacccaa gcgatctgga gagcggcggg ctgctgcatg agattttcac gtcgccgctc aacctgctgc tgcttggcct ctgcatcttc ctgctctaca agatcgtgcg cggggaccag ccggcggcca gcggcgacag cgacgacgac gagccgcccc ctctgccccg cctcaagcgg cgcgacttca cccccgccga gctgcggcgc ttcgacggcg tccaggaccc gcgcatactc atggccatca acggcaaggt gttcgatgtg accaaaggcc gcaaattcta cgggcccgag gggccgtatg gggtctttgc tggaagagat gcatccaggg gccttgccac attttgcctg gataaggaag cactgaagga tgagtacgat gacctttctg acctcactgc tgcccagcag gagactctga gtgactggga gtctcagttc actttcaagt atcatcacgt gggcaaactg ctgaaggagg gggaggagcc cactgtgtac tcagatgagg aagaaccaaa agatgagagt gcccggaaaa atgattaa.
```

An example of a polypeptide sequence for human PGR is GenBank Accession No. NP_000917:

```
                                            (SEQ ID NO: 5)
MTELKAKGPR APHVAGGPPS PEVGSPLLCR PAAGPFPGSQ

TSDTLPEVSA IPISLDGLLFPRPCQGQDPS DEKTQDQQSL

SDVEGAYSRA EATRGAGGSS SSPPEKDSGL

LDSVLDTLLAPSGPGQSQPS PPACEVTSSW CLFGPELPED

PPAAPATQRV LSPLMSRSGC KVGDSSGTAAAHKVLPRGLS

PARQLLLPAS ESPHWSGAPV KPSPQAAAVE VEEEDGSESE

ESAGPLLKGKPRALGGAAAG GGAAAVPPGA AAGGVALVPK

EDSRFSAPRV ALVEQDAPMA PGRSPLATTVMDFIHVPILP

LNHALLAART RQLLEDESYD GGAGAASAFA PPRSSPCASS

TPVAVGDFPDCAYPPDAEPK DDAYPLYSDF QPPALKIKEE

EEGAEASARS PRSYLVAGAN PAAFPDFPLGPPPPLPPRAT

PSRPGEAAVT AAPASASVSS ASSSGSTLEC ILYKAEGAPP

QQGPFAPPPCKAPGASGCLL PRDGLPSTSA SAAAAGAAPA

LYPALGLNGL PQLGYQAAVL KEGLPQVYPPYLNYLRPDSE

ASQSPQYSFE SLPQKICLIC GDEASGCHYG VLTCGSCKVF

FKRAMEGQHNYLCAGRNDCI VDKIRRKNCP ACRLRKCCQA

GMVLGGRKFK KFNKVRVVRA LDAVALPQPVGVPNESQALS

QRFTFSPGQD IQLIPPLINL LMSIEPDVIY AGHDNTKPDT

SSSLLTSLNQLGERQLLSVV KWSKSLPGFR NLHIDDQITL

IQYSWMSLMV FGLGWRSYKH VSGQMLYFAPDLILNEQRMK

ESSFYSLCLT MWQIPQEFVK LQVSQEEFLC MKVLLLLNTI

PLEGLRSQTQFEEMRSSYIR ELIKAIGLRQ KGVVSSSQRF

YQLTKLLDNL HDLVKQLHLY CLNTFIQSRA LSVEFPEMMS

EVIAAQLPKI LAGMVKPLLF HKK.
```

An example of a nucleotide sequence for human PGRMC1 mRNA is GenBank Accession No. NM_000926:

(SEQ ID NO: 6)
```
agtccacagc tgtcactaat cggggtaagc cttgttgtat
ttgtgcgtgt gggtggcatt ctcaatgaga actagcttca
cttgtcattt gagtgaaatc tacaacccga ggcggctagt
gctcccgcac tactgggatc tgagatcttc ggagatgact
gtcgcccgca gtacggagcc agcagaagtc cgaccttcc
tgggaatggg ctgtaccgag aggtccgact agcccaggg
ttttagtgag ggggcagtgg aactcagcga gggactgaga
gcttcacagc atgcacgagt ttgatgccag agaaaaagtc
gggagataaa ggagccgcgt gtcactaaat tgccgtcgca
gccgcagcca ctcaagtgcc ggacttgtga gtactctgcg
tctccagtcc tcggacagaa gttggagaac tctcttggag
aactccccga gttaggagac gagatctcct aacaattact
acttttctt gcgctcccca cttgccgctc gctgggacaa
acgacagcca cagttcccct gacgacagga tggaggccaa
gggcaggagc tgaccagcgc cgccctcccc cgccccgac
ccaggaggtg gagatcctc cggtccagc acattcaaca
cccactttct cctccctctg ccctatatt cccgaaaccc
cctcctcctt cccttttccc tcctcctgga gacggggag
gagaaaaggg gagtccagtc gtcatgactg agctgaaggc
aaagggtccc cgggctcccc acgtggcggg cggcccgcc
tcccccgagg tcggatcccc actgctgtgt cgcccagccg
caggtccgtt cccggggagc cagacctcgg acaccttgcc
tgaagtttcg gccataccta tctccctgga cgggctactc
ttccctcggc cctgccaggg acaggaccc tccgacgaaa
agacgcagga ccagcagtcg ctgtcggacg tggagggcgc
atattccaga gctgaagcta caaggggtgc tggaggcagc
agttctagtc ccccagaaaa ggacagcgga ctgctggaca
gtgtcttgga cactctgttg gcgcccctcag gtcccgggca
gagccaaccc agccctcccg cctgcgaggt caccagctct
tggtgcctgt ttggccccga acttcccgaa gatccaccgg
ctgcccccgc cacccagcgg gtgttgtccc cgctcatgag
ccggtccggg tgcaaggttg gagacagctc cgggacggca
gctgcccata aagtgctgcc ccggggcctg tcaccagccc
ggcagctgct gctcccggcc tctgagagcc ctcactggtc
cggggcccca gtgaagccgt ctccgcaggc cgctgcggtg
gaggttgagg aggaggatgg ctctgagtcc gaggagtctg
cgggtccgct tctgaaggcc aaacctcggg ctctgggtgg
cgcggcggct ggaggaggag ccgcggctgt cccgccgggg
gcggcagcag gaggcgtcgc cctggtcccc aaggaagatt
cccgcttctc agcgcccagg gtcgccctgg tggagcagga
cgcgccgatg gcgcccgggc gctccccgct ggccaccacg
gtgatggatt tcatccacgt gcctatcctg cctctcaatc
acgccttatt ggcagcccgc actcggcagc tgctggaaga
cgaaagttac gacggcgggg ccggggctgc cagcgccttt
gccccgccgc ggagttcacc ctgtgcctcg tccacccgg
tcgctgtagg cgacttcccc gactgcgcgt acccgcccga
cgccgagccc aaggacgacg cgtaccctct ctatagcgac
ttccagccgc ccgctctaaa gataaaggag gaggaggaag
gcgcggaggc ctccgcgcgc tccccgcgtt cctaccttgt
ggccggtgcc aaccccgcag ccttcccgga tttcccgttg
gggccaccgc ccccgctgcc gccgcgagcg accccatcca
gacccgggga agcggcggtg acggccgcac ccgccagtgc
ctcagtctcg tctgcgtcct cctcggggtc gaccctggag
tgcatcctgt acaaagcgga gggcgcgccg cccagcagg
gcccgttcgc gccgccgccc tgcaaggcgc cgggcgcgag
cggctgcctg ctcccgcggg acggcctgcc ctccacctcc
gcctctgccg ccgccgccgg ggcggccccc gcgctctacc
ctgcactcgg cctcaacggg ctcccgcagc tcggctacca
ggccgccgtg ctcaaggagg gcctgccgca ggtctacccg
ccctatctca actacctgag gccggattca gaagccagcc
agagcccaca atacagcttc gagtcattac ctcagaagat
ttgtttaatc tgtggggatg aagcatcagg ctgtcattat
ggtgtcctta cctgtgggag ctgtaaggtc ttctttaaga
gggcaatgga agggcagcac aactacttat gtgctggaag
aaatgactgc atcgttgata aaatccgcag aaaaaactgc
ccagcatgtc gccttagaaa gtgctgtcag gctggcatgg
tccttggagg tcgaaaattt aaaaagttca ataaagtcag
agttgtgaga gcactggatg ctgttgctct cccacagcca
gtgggcgttc caaatgaaag ccaagcccta agccagagat
tcacttttc accaggtcaa gacatacagt tgattccacc
actgatcaac ctgttaatga cattgaacc agatgtgatc
tatgcaggac atgacaacac aaaacctgac acctccagtt
ctttgctgac aagtcttaat caactaggcg agaggcaact
tctttcagta gtcaagtggt ctaaatcatt gccaggtttt
cgaaacttac atattgatga ccagataact ctcattcagt
attcttggat gagcttaatg gtgtttggtc taggatggag
atcctacaaa cacgtcagtg gcagatgct gtattttgca
cctgatctaa tactaaatga acagcggatg aaagaatcat
cattctattc attatgcctt accatgtggc agatcccaca
```

-continued

```
ggagtttgtc aagcttcaag ttagccaaga agagttcctc
tgtatgaaag tattgttact tcttaataca attcctttgg
aagggctacg aagtcaaacc cagtttgagg agatgaggtc
aagctacatt agagagctca tcaaggcaat tggtttgagg
caaaaaggag ttgtgtcgag ctcacagcgt ttctatcaac
ttacaaaact tcttgataac ttgcatgatc ttgtcaaaca
acttcatctg tactgcttga atacatttat ccagtcccgg
gcactgagtg ttgaatttcc agaaatgatg tctgaagtta
ttgctgcaca attacccaag atattggcag ggatggtgaa
accccttctc tttcataaaa agtgaatgtc atcttttttct
tttaaagaat taaattttgt ggtatgtctt tttgttttgg
tcaggattat gaggtcttga gttttttataa tgttcttctg
aaagccttac atttataaca tcatagtgtg taaatttaaa
agaaaaattg tgaggttcta attattttct tttataaagt
ataattagaa tgtttaactg ttttgtttac ccatatttc
ttgaagaatt tacaagattg aaaaagtact aaaattgtta
aagtaaacta tcttatccat attatttcat accatgtagg
tgaggatttt taacttttgc atctaacaaa tcatcgactt
aagagaaaaa atcttacatg taataacaca aagctattat
atgttatttc taggtaactc ccttttgtgtc aattatatttt
ccaaaaatga acctttaaaa tggtatgcaa aattttgtct
atatatattt gtgtgaggag gaaattcata actttcctca
gattttcaaa agtattttta atgcaaaaaa tgtagaaaga
gtttaaaacc actaaaatag attgatgttc ttcaaactag
gcaaaacaac tcatatgtta agaccatttt ccagattgga
aacacaaatc tcttaggaag ttaataagta gattcatatc
attatgcaaa tagtattgtg ggttttgtag gttttttaaaa
taacctttt tggggagaga attgtcctct aatgaggtat
tgcgagtgga cataagaaat cagaagatta tggcctaact
gtactcctta ccaactgtgg catgctgaaa gttagtcact
cttactgatt ctcaattctc tcacctttga aagtagtaaa
atatctttcc tgccaattgc tcctttgggt cagagcttat
taacatcttt tcaaatcaaa ggaaagaaga aagggagagg
aggaggaggg aggtatcaat tcacatacct ttctcctctt
tatcctccac tatcatgaat tcatattatg tttcagccat
gcaaatcttt ttaccatgaa atttcttcca gaattttccc
cctttgacac aaattccatg catgtttcaa ccttcgagac
tcagccaaat gtcatttctg taaaatcttc cctgagtctt
ccaagcagta atttgccttc tcctagagtt tacctgccat
tttgtgcaca tttgagttac agtagcatgt tattttacaa
```

```
ttgtgactct cctgggagtc tgggagccat ataaagtggt
caatagtgtt tgctgactga gagttgaatg acattttctc
tctgtcttgg tattactgta gatttcgatc attctttggt
tacatttctg catatttctg tacccatgac tttatcactt
tcttctccca tgctttatct ccatcaatta tcttcattac
ttttaaattt tccacctttg cttcctactt tgtgagatct
ctcccttttac tgactataac atagaagaat agaagtgtat
tttatgtgtc ttaaggacaa tactttagat tccttgttct
aagtttttaa actgaatgaa tggaatatta tttctctccc
taagcaaaat tccacaaaac aattatttct tatgtttatg
tagccttaaa ttgttttgta ctgtaaacct cagcataaaa
actttcttca tttctaattt cattcaacaa atattgattg
aatacctggt attagcacaa gaaaaatgtg ctaataagcc
ttatgagaat ttggagctga agaaagacat ataactcagg
aaagttacag tccagtagta ggtataaatt acagtgcctg
ataaataggc atttttaatat ttgtacactc aacgtatact
aggtaggtgc aaaacattta catataattt tactgatacc
catgcagcac aaaggtacta actttaaata ttaaataaca
cctttatgtg tcagtaattc atttgcatta aatcttattg
aaaaggcttt caatatattt tccccacaaa tgtcatccca
agaaaaaagt attttttaaca tctcccaaat ataatagtta
caggaaatct acctctgtga gagtgacacc tctcagaatg
aactgtgtga cacaagaaaa tgaatgtagg tctatccaaa
aaaaacccca agaaacaaaa acaatattat tagccccttta
tgcttaagtg atggactcag ggaacagttg atgttgtgat
cattttatta tctgattctt gttactttga attaaaccaa
tattttgatg atataaatca tttccaccag catatattta
atttccataa taacttttaaa attttctaat ttcactcaac
tatgagggaa tagaatgtgg tggccacagg tttggctttt
gttaaaatgt ttgatatctt cgatgttgat ctctgtctgc
aatgtagatg tctaaacact aggatttaat atttaaggct
aagctttaaa aataaagtac cttttttaaaa agaatatggc
ttcaccaaat ggaaaatacc taatttctaa atcttttttct
ctacaaagtc ctatctacta atgtctccat tactatttag
tcatcataac cattatcttc attttacatg tcgtgttctt
tctggtagct ctaaaatgac actaaatcat aagaagacag
gttacatatc aggaaatact tgaaggttac tgaaatagat
tcttgagtta atgaaaatat tttctgtaaa aaggtttgaa
aagccatttg agtctaaagc attataccte cattatcagt
agttatgtga caattgtgtg tgtgtttaat gtttaaagat
gtggcacttt ttaataaggc aatgctatgc tatttttttcc
```

-continued

```
catttaacat taagataatt tattgctata cagatgatat
ggaaatatga tgaacaatat ttttttttgcc aaaactatgc
cttgtaagta gccatggaat gtcaacctgt aacttaaatt
atccacagat agtcatgtgt ttgatgatgg gcactgtgga
gataactgac ataggactgt gccccccttc tctgccactt
actagctgga tgagattaag caagtcattt aactgctctg
attaaacctg cctttcccaa gtgctttgta atgaatagaa
atggaaacca aaaaaaacgt atacaggcct tcagaaatag
taattgctac tattttgttt tcattaagcc atagttctgg
ctataatttt atcaaactca ccagctatat tctacagtga
aagcaggatt ctagaaagtc tcactgtttt atttatgtca
ccatgtgcta tgatatattt ggttgaattc atttgaaatt
agggctggaa gtattcaagt aatttcttct gctgaaaaaa
tacagtgttt tgagtttagg cctgttttta tcaaagttct
aaagagccta tcactcttcc attgtagaca ttttaaaata
atgacactga ttttaacatt tttaagtgtc tttttagaac
agagagcctg actagaacac agcccctcca aaaacccatg
ctcaaattat ttttactatg gcagcaattc cacaaagggg
aacaatgggt ttagaaatta caatgaagtc atcaacccaa
aaaacatccc tatccctaag aaggttatga tataaaatgc
ccacaagaaa tctatgtctg ctttaatctg tcttttattg
ctttggaagg atggctatta cattttagt ttttgctgtg
aatacctgag cagtttctct catccatact tatccttcac
acatcagaag tcaggataga atatgaatca ttttaaaaac
ttttacaact ccagagccat gtgcataaga agcattcaaa
acttgccaaa acatacattt tttttcaaat ttaaagatac
tctattttg tattcaatag ctcaacaact gtggtcccca
ctgataaagt gaagtggaca aggagacaag taatggcata
agtttgtttt tcccaaagta tgcctgttca atagccattg
gatgtgggaa atttctacat ctcttaaaat tttacagaaa
atacatagcc agatagtcta gcaaagttc accaagtcct
aaattgctta tccttacttc actaagtcat gaaatcattt
taatgaaaag aacatccct aggttttgtg gtttcttttt
ttcttattca tggctgagtg aaaacaacaa tctctgtttc
tccctagcat ctgtggacta tttaatgtac cattattcca
cactctatgg tccttactaa atacaaaatt gaacaaaaag
cagtaaaaca actgactctt cacccatatt ataaaatata
atccaagcca gattagtcaa catccataag atgaatccaa
gctgaactgg gcctagatta ttgagttcag gttggatcac
atccctattt attaataaac ttaggaaaga aggccttaca
```

-continued

```
gaccatcagt tagctggagc taatagaacc tacacttcta
aagttcggcc tagaatcaat gtggccttaa aagctgaaaa
gaagcaggaa agaacagttt tcttcaataa tttgtccacc
ctgtcactgg agaaaattta agaatttggg ggtgttggta
gtaagttaaa cacagcagct gttcatggca gaaattattc
aatacatacc ttctctgaat atcctataac caaagcaaag
aaaaacacca aggggtttgt tctcctcctt ggagttgacc
tcattccaag gcagagctca ggtcacaggc acaggggctg
cgcccaagct tgtccgcagc cttatgcagc tgtggagtct
ggaagactgt tgcaggactg ctggcctagt cccagaatgt
cagcctcatt ttcgattac tggctcttgt tgctgtatgt
catgctgacc ttattgttaa acacaggttt gttttgctttt
tttccactca tggagacatg ggagaggcat tatttttaag
ctggttgaaa gctttaaccg ataaagcatt tttagagaaa
tgtgaatcag gcagctaaga aagcatactc tgtccattac
ggtaaagaaa atgcacagat tattaactct gcagtgtggc
attagtgtcc tggtcaatat tcgatagat atgaataaaa
tatttaaatg gtattgtaaa tagttttcag gacatatgct
atagcttatt tttattatct tttgaaattg ctcttaatac
atcaaatcct gatgtattca atttatcaga tataaattat
tctaaatgaa gcccagttaa atgtttttgt cttgtcagtt
atatgttaag tttctgatct cttttgtctat gacgtttact
aatctgcatt tttactgtta tgaattattt tagacagcag
tggtttcaag cttttttgcca ctaaaaatac cttttatttt
ctcctccccc agaaaagtct ataccttgaa gtatctatcc
accaaactgt acttctatta agaaatagtt attgtgtttt
cttaatgttt tgttattcaa agacatatca atgaaagctg
ctgagcagca tgaataacaa ttatatccac acagatttga
tatatttgt gcagccttaa cttgatagta taaaatgtca
ttgctttta aataatagtt agtcaatgga cttctatcat
agcttccta aactaggtta agatccagag ctttggggtc
ataatatatt acatacaatt aagttatctt tttctaaggg
cttaaaatt catgagaata accaaaaaag gtatgtggag
agttaataca aacataccat attcttgttg aaacagagat
gtggctctgc ttgttctcca taaggtagaa atactttcca
gaatttgcct aaaactagtaa gccctgaatt tgctatgatt
agggatagga agagattttc acatggcaga ctttagaatt
cttcacttta gccagtaaag tatctccttt tgatcttagt
attctgtgta ttttaacttt tctgagttgt gcatgtttat
aagaaaaatc agcacaaagg gtttaagtta aagccttttt
actgaaattt gaaagaaaca gaagaaaata tcaaagttct
```

-continued

```
ttgtattttg agaggattaa atatgattta caaaagttac
atggagggct ctctaaaaca ttaaattaat tatttttgt
tgaaaagtct tactttaggc atcattttat tcctcagcaa
ctagctgtga agcctttact gtgctgtatg ccagtcactc
tgctagattg tggagattac cagtgttccc gtcttctccg
agcttagagt tggatgggga ataaagacag gtaaacagat
agctacaata ttgtactgtg aatgcttatg ctggaggaag
tacagggaac tattggagca cctaagagga gcacctacct
tgaatttagg ggttagcaga ggcatcctga aaaaagtcaa
agctaagcca caatctaaa gcagtttagg aattagcaga
acgtgcgtgg tgaggagatg ccaaaggcaa gaagagaaga
gtattccaaa caggagggat tccaaagaga gaagagtatc
ccaaacaaca tttgcacaaa cctgatgggg agagagaatg
tgggtgggg atggatgatg agactgaaga agaaagccag
gtctagataa tcagtggcct tgtacaccat gttaaagagt
gtagacttga ttctgttgta aacaggaaag cagcacaatt
catatgaata ttttagaaga ctcccactgg aatatggaga
ataaagttgg agatgactaa tcctggaagc agggagaaca
tttttgagga agttgcacta ttttggtgaa aatgatgatc
ataaacatga agaattgtag gtgatcatga cctcctctct
aattttccag aagggttttg gaagatataa cataggaaca
ttgacaggac tgacgaaagg agatgaaata caccatataa
attgtcaaac acaaggccag atgtctaatt attttgctta
tgtgttgaaa ttacaaattt ttcatcagga aaccaaaaac
tacaaaactt agttttccca agtcccagaa ttctatctgt
ccaaacaatc tgtaccactc cacctatatc cctacctttg
catgtctgtc caacctcaaa gtccaggtct atacacacgg
gtaagactag agcagttcaa gtttcagaaa atgagaaaga
ggaactgagt tgtgctgaac ccatacaaaa taaacacatt
ctttgtatag attcttggaa cctcgagagg aattcaccta
actcataggt atttgatggt atgaatccat ggctgggctc
ggcttttaaa aagccttatc tgggattcct tctatggaac
caagttccat caaagcccat ttaaaagcct acattaaaaa
caaaattctt gctgcattgt atacaaataa tgatgtcatg
atcaaataat cagatgccat tatcaagtgg aattacaaaa
tggtataccc actccaaaaa aaaaaaaaaa gctaaattct
cagtagaaca ttgtgacttc atgagccctc cacagccttg
gagctgagga gggagcactg gtgagcagta ggttgaagag
aaaacttggc gcttaataat ctatccatgt ttttcatct
aaaagagcct tcttttttgga ttaccttatt caatttccat
caaggaaatt gttagttcca ctaaccagac agcagctggg
aaggcagaag cttactgtat gtacatggta gctgtgggaa
ggaggtttct ttctccaggt cctcactggc catacaccag
tcccttgtta gttatgcctg gtcatagacc cccgttgcta
tcatctcata tttaagtctt tggcttgtga atttatctat
tctttcagct tcagcactgc agagtgctgg gactttgcta
acttccattt cttgctggct tagcacattc ctcataggcc
cagctctttt ctcatctggc cctgctgtgg agtcaccttg
cccccttcagg agagccatgg cttaccactg cctgctaagc
ctccactcag ctgccaccac actaaatcca gcttctcta
agatgttgca gactttacag gcaagcataa aaggcttgat
cttcctggac ttccctttac ttgtctgaat ctcacctcct
tcaactttca gtctcagaat gtaggcattt gtcctctttg
ccctacatct tccttcttct gaatcatgaa agcctctcac
ttcctcttgc tatgtgctgc aggcttctgt caggttttag
aatgagttct catctagtcc tagtagcttt tgatgcttaa
gtccacctt taaggatacc tttgagattt agaccatgtt
tttcgcttga gaaagcccta atctccagac ttgcctttct
gtggatttca aagaccaact gaggaagtca aaagctgaat
gttgactttc tttgaacatt tccgctataa caattccaat
tctcctcaga gcaatatgcc tgcctccaac tgaccaggag
aaaggtccag tgccaaagag aaaaacacaa agattaatta
tttcagttga gcacatactt tcaaagtggt ttgggtattc
atatgaggtt ttctgtcaag agggtgagac tcttcatcta
tccatgtgtg cctgacagtt ctcctggcac tggctggtaa
cagatgcaaa actgtaaaaa ttaagtgatc atgtattta
acgatatcat cacatactta ttttctatgt aatgttttaa
atttcccta acatactttg actgttttgc acatggtaga
tattcacatt tttttgtgtt gaagttgatg caatcttcaa
agttatctac cccgttgctt attagtaaaa ctagtgttaa
tacttggcaa gagatgcagg gaatctttct catgactcac
gccctattta gttattaatg ctactaccct attttgagta
agtagtaggt ccctaagtac attgtccaga gttatacttt
taaagatatt tagccccata tacttcttga atctaaagtc
atacaccttg ctcctcattt ctgagtggga aagacatttg
agagtatgtt gacaattgtt ctgaaggttt ttgccaagaa
ggtgaaactg tcctttcatc tgtgtatgcc tggggctggg
tccctggcag tgatggggtg acaatgcaaa gctgtaaaaa
ctaggtgcta gtgggcacct aatatcatca tcatatactt
attttcaagc taatatgcaa aatcccatct ctgttttaa
actaagtgta gatttcagag aaaatatttt gtggttcaca
```

-continued

```
taagaaaaca gtctactcag cttgacaagt gttttatgtt aaattggctg gtggtttgaa atgaatcatc ttcacataat gttttcttta aaaatattgt gaatttaact ctaattcttg ttattctgtg tgataataaa gaataaacta atttcta
```

As described herein, PGRMC1 siRNAs can be used in the methods of the invention, for example, to treat ovarian cancer as described herein. The skilled artisan will know how to select appropriate commercially available PGRMC1 or how to generate such siRNAs for use in the methods described herein. Examples of commercially available PGRMC1 siRNA sequences that can be used in the methods described herein include, e.g., PGRMC1 siRNAs available from Ambion, for example:

Ambion siRNA ID #18248 (which targets Exon 1, nucleotides 365-386):

```
                                   (SEQ ID NO: 7)
Forward 5'-GGUGUUCGAUGUGACCAAAtt-3'
and
                                   (SEQ ID NO: 8)
Reverse 5'-UUUGGUCACAUCGAACACCtt-3';
```

Ambion siRNA ID #18340 (which targets Exon 2, nucleotides 473 to 494):

```
                                   (SEQ ID NO: 9)
Forward 5'-GGAAGCACUGAAGGAUGAGtt-3'
and
                                   (SEQ ID NO: 10)
Reverse 5'-CUCAUCCUUCAGUGCUUCCtt-3';
and
```

Ambion siRNA ID #18430 (which targets Exon 3, nucleotides 1020 to 1041):

```
                                   (SEQ ID NO: 11)
Forward 5'-GGAUCAACUUUUAGUCAUGtt-3'
and
                                   (SEQ ID NO: 12)
Reverse 5'-CAUGACUAAAAGUUGAUCCtt-3'.
```

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

PGRMC1 Mediates Progesterone's Anti-Apoptotic Effect

Experiments with human granulosa/luteal cells were conducted by using the methods as described in detail below or, in instances where only brief descriptions are provided below, by using methods that have been published and are well known in the field.

Patients

Granulosa/luteal cells were obtained by follicular aspiration from women with various infertility diagnoses undergoing in vitro fertilization under a protocol approved by the Institutional Review Board of the University of Connecticut Health Center. Briefly, patients were treated with a GnRH (gonadotropin releasing hormone) analog (Lupron) during the luteal phase to suppress ovarian function (i.e. estradiol levels of <75 pg/ml and no follicles>10 mm). Once ovarian function was suppressed then the patients were treated with gonadotropins as outlined by Schmidt et al. Patients that have two to three follicles with an 18 mm average diameter and estradiol values of between 2500 and 5,500 pg/ml were injected with human chorionic gonadotropin (hCG). Thirty-five hours after hCG administration, the follicles were aspirated under transvaginal ultrasound guidance.

Cell Preparation and Culture

After the oocytes were removed, follicular aspirates were pooled and centrifuged at 250×g for 10 minutes. The cell pellet was resuspended in serum-free culture medium, layered on HISTOPAQUE-1077 and centrifuged for 30 minutes at 400×g. After centrifugation, the opaque interface containing the granulosa/luteal cells was carefully aspirated and transferred into a 15 ml sterile conical centrifuge tube. The cells were then washed by resuspending the cells in 12 ml of PBS and centrifuging them at 250×g for 10 minutes. This was repeated two additional times. The cell pellet was then resuspended in 1 ml of 0.25% trypsin-EDTA solution and incubated for 5 minutes to dissociate the cells. After trypsinization, 5 ml of serum-supplemented medium was added and the cells were centrifuged at 250×g for 10 minutes. The cells were then resuspended in serum-supplemented medium, counted in a hemacytometer and resuspended to yield a final concentration 1 million cells/ml.

Plastic lab-tek slides (BD Bioscience, Bedford, Mass.), which had been previously coated with Growth Factor Reduced Matrigel Matrix (BD Bioscience, Bedford, Mass.), were plated at about 60,000 cells per well in 0.5 ml of serum-supplemented medium with 2 U/ml (IU) of hCG. The medium was changed after 24 hours to remove any remaining blood cells or non-attached granulosa/luteal cells and the cultures continued for two additional days. The cultures were then subjected to the various experimental treatments as outlined below.

Detection of Apoptotic Nuclei

Both TUNEL and in situ DNA staining were used to identify apoptotic nuclei. For the TUNEL assay human granulosa/luteal cells were cultured for 5 hours in serum-free medium and then fixed in 10% formalin. The cells were stained using the Apoptag Peroxidase In Situ kit staining according to manufacture's instructions (Chemicon, Temecula, Calif.). In situ DNA staining was done by adding hydroethidine directly to the culture medium at a final concentration of 3.5 µg/ml. The cultures were incubated for 15 minutes at room temperature in the dark. After staining, the cells observed under epi-fluorescent optics. Under these conditions only cells with condensed or fragmented nuclei were stained intensely with hydroethidine. These cells were considered to be apoptotic in accordance with prior publications in the field. At least 100 cells/culture well were counted and the percentage of apoptotic nuclei in each well determined.

Immunocytochemical and Western Blot Analysis

To localize the Progesterone Receptor (PGR), cells were fixed with 10% formalin and permeabilized with 0.1% Triton-X. Endogenous peroxidase activity was blocked by incubating the cells in 0.3% peroxidase in methanol for 30 minutes at room temperature. To reduce non-specific staining, the slides were incubated with powerblock (Biogenex, San Roman, Calif.) and then incubated overnight with a 1:50 dilution of PGR antibody (Ab-8, Lab Vision/Neomarker, Fremont, Calif.). The cells were then incubated with biotinylated goat anti-rabbit IgG followed by incubation for 30 minutes with ABC reagent (Vector Laboratories, Burlingame, Calif.). The slides were developed using a diaminobenzidine-peroxidase substrate for 5 minutes followed by light counter-staining with Methyl Green. The presence of PGR was revealed by the presence of a reddish-brown precipitate.

Expression and localization of PGRMC1 and PAIRBP1 was assessed by Western blot and confocal immunocytochemistry, respectively. For Western blot studies, human granulosa/luteal cells were lysed in RIPA buffer (50 mM TRIS, 150 mM sodium chloride, 1.0 mM EDTA, 1% Nonidet progesterone and 0.25% sodium-deoxycolate; pH 7.0) which was supplemented with complete protease inhibitor cocktail (Roche, Mannheim, Germany) and phosphatase inhibitor cocktail 1 (Sigma Chemical Co., St Louis, Mo.) and then centrifuged at 1,000×g at 4° C. for 5 minutes. The supernatant was collected and centrifuged at 100,000×g at 4° C. for 1 hour. Twenty µg of this membrane preparation was run on a 12% acrylamide gel and transferred to nitrocellulose. The nitrocellulose was then incubated with 5% non-fat dry milk overnight at 4° C. The nitrocellulose blot was then incubated with either the chicken PAIRBP1 antibody at a dilution of 1:2000 or the rabbit PGRMC1-NT antibody (1:2000) (published method) for 1 hour at room temperature. Western blots were processed using a horseradish peroxidase goat anti-chicken IgY (1:50,000; Aves Labs, Tigard, Oreg.) or a horseradish peroxidase goat anti-mouse antibody (1:10,000). KPL LumiGlo detection system was used to reveal the presence of both proteins. As a negative control, an immunodepleted antibody preparation or rabbit IgG was used in place of the PAIRBP1 antibody and PGRMC1-NT antibody, respectively.

For confocal studies human granulosa/luteal cells were grown on glass coverslips within 35 mm culture dishes. After three days of culture these cells were washed and then fixed in 10% formalin and permeabilized as previously described (published method). The coverslips were then incubated overnight at 4° C. with the antibodies to PAIRBP1 (1:50), PGRMC1-NT (1:50) or both. After washing to remove the primary antibodies, the coverslips were incubated for 1 hour at room temperature in the dark with Alexa Fluor 633-goat anti-chicken IgG (1:100) and Alexa Fluor 488-goat anti-rabbit IgG (1:100). The coverslips were again washed and observed under the confocal microscopy. Negative controls were also processed as described above with the exception that the immunodepleted antibody preparation or IgG was used in place of the PAIRBP1 or PGRMC1-NT antibody, respectively.

PGRMC1 and PAIRBP1 Blocking Antibody Study

Human granulosa/luteal cells were plated on lab tek slides and cultured for three days as previously described. The cells were then washed in serum-free medium and cultured for one hour with either serum-free media supplemented with rabbit IgG (20 µg/ml), antibody to PGRMC1 (20 µg/ml), IgY (34 µg/ml) or an antibody to PAIRBP1 (34 µg/ml) in the presence or absence of progesterone (0.1 µM). After culture the cells were raised in Krebs/Hepes buffer and stained to detect apoptotic nuclei as taught by Engmann et al., *J. of Clinical Endocrinology and Metabolism* 91(12): 4962-4968 (2006). One hundred cells in each chamber were counted and the percentage of apoptotic nuclei determined as previously described.

Statistical Analysis

All experiments were repeated at least three times with each experiment yielding essentially identical results. When appropriate, the data were pooled to generate means±standard errors and analyzed by either a Student $^3t^2$ tests when an experiment consisted of two treatment groups or a one-way ANOVA followed by a Student-Newman-Keuls test, if more than two treatments groups were being compared. P values of less than 0.05 were considered to be significant.

Serum withdrawal induced human granulosa/luteal cells to rapidly undergo apoptosis as assessed by both TUNEL assay and in situ DNA staining. About 10% of the human granulosa/luteal cells maintained in serum-supplemented medium for three days were considered to be apoptotic. This percentage increased to about 30% within five hours of serum withdrawal (p<0.05). Time-course studies revealed that a similar increase in apoptosis was observed after one hour in serum-free medium and that this increase was suppressed by progesterone. Moreover, progesterone at all doses tested suppressed apoptosis. The lowest effective dose was 10 nM.

Immunocytochemical analysis revealed that after three days of culture about 20% of the human granulosa/luteal cells expressed the PGR. Moreover, 25 and 50 µM doses of the PGR antagonist, RU486, increased the percentage of apoptotic nuclei to greater than 70%. Progesterone at 1 µM could not override the effect of RU486 at these high concentrations. Interestingly, 5 µM RU486 did not increase the percentage of apoptotic nuclei compared to control and 1 µM progesterone was still capable of suppressing serum-withdrawal induced apoptosis. Finally, when human granulosa/luteal cells were deprived of progesterone for 15 or 30 minutes, progesterone's ability to prevent apoptosis was lost.

Figure 2:
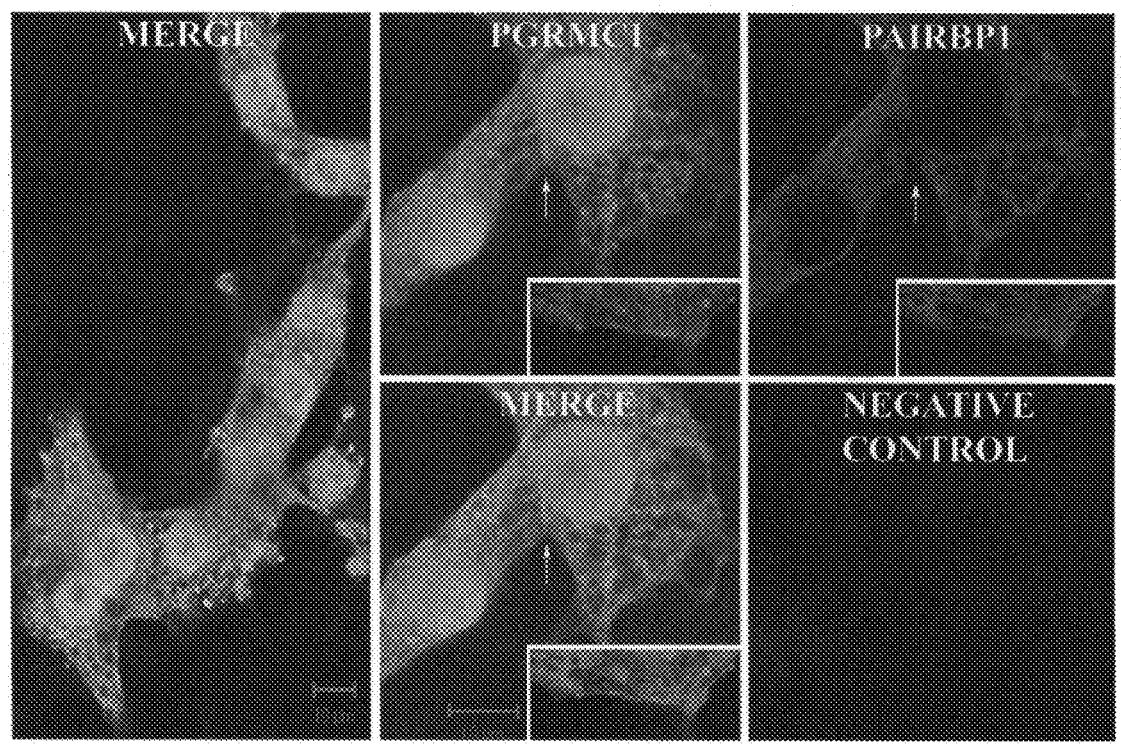
FIG. 2 is a scan of a micrograph showing immunocytochemical localization of PGRMC1 and PAIRBP1 in human granulosa/luteal cells after three days of culture. The presence of PGRMC1 was revealed by a green fluorescence, while PAIRBP1 was detected by a red fluorescence. The yellow-orange fluorescence in the panels labeled MERGE reveals cellular sites where the two proteins co-localize. The panel on the left shows several human granulosa/luteal cells with all cells expressing both PGRMC1 and PAIRBP1. The insert shows a higher magnification of the periphery of a single human granulosa/luteal cell.

Western blot and confocal analysis revealed that both of these proteins were expressed in human granulosa/luteal cells (FIGS. 1 and 2, respectively). Unlike PGR expression, virtually all the human granulosa/luteal cells expressed PGRMC1 and PAIRBP1 (FIG. 2). These proteins co-localized near the plasma membrane as well as to a fibrous network within the cytoplasm (FIG. 2). Although these proteins were often co-localized, PGRMC1 did not appear to associate with PAIRBP1 at the points of cell-cell contact or in the nucleus (FIG. 2). The nuclear localization of PGRMC1 was particularly intense. Note that the exclusive localization of PGRMC1 to the areas of cell-cell contact that is illustrated in the higher magnification merged image (arrow) is not clearly seen in the lower magnification merged image. This is because the cells do not form a flat monolayer and it is impossible to observe all the cells in the precise focal plane that reveals the localization of PGRMC1 to the site of cell-cell contact.

Figure 3:
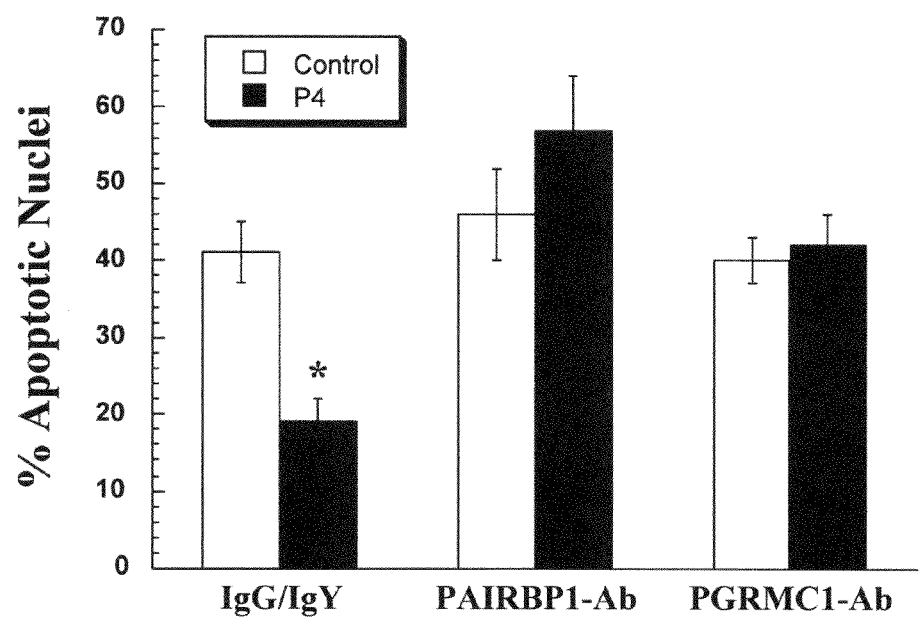
FIG. 3 is a bar graph of percent apoptotic nuclei showing the effect of PAIRBP1 and PGRMC1 antibodies on progesterone's anti-apoptotic action in human granulosa/luteal cells. In this experiment progesterone was used at 0.1 µM. Values in this graph are means±SE of eight replicate cultures taken from 6 patients. The asterisk indicates a value that is different from the IgG/IgY control (p<0.05). The rate of apoptosis was assessed after one hour of culture.

In the presence of either IgG or IgY, 1 µM progesterone suppressed apoptosis due to serum-withdrawal. In contrast, antibodies to either PAIRBP1 or PGRMC1 completely attenuated progesterone's anti-apoptotic action in human granulosa/luteal cells (FIG. 3).

Example 2

Expression Of PGRMC1 And PAIRBP1 in Human Ovarian Cancer Tissues

Figure 4:
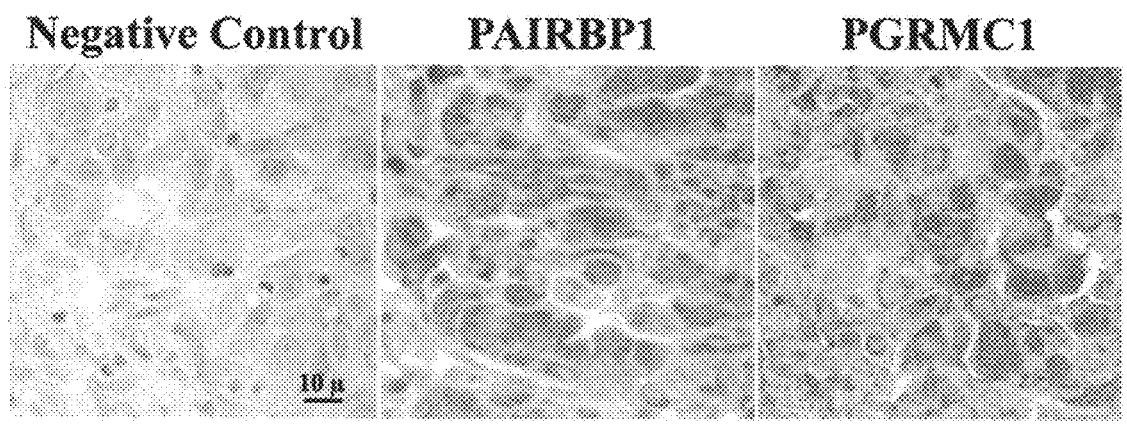
FIG. 4 is a reproduction of micrographs showing expression of PAIRBP1 (middle panel) and PGRMC1 (right panel) in ovarian cancer as assessed by immunohistochemistry. Each protein is revealed by the presence of a brown stain. A negative control is shown in the left panel.

Tissues were obtained from patients with Stage 1V ovarian epithelial cell cancer and immunohistochemical studies were conducted as described above. Both PGRMC1 and PAIRBP1 are expressed in ovarian epithelial cancer cells (FIG. 4).

Example 3

Expression Of PGRMC1 in Human Ovarian Cancer Tissues Not Expressing PGR

Tissues were obtained from patients with Stage III ovarian epithelial cell cancer and immunohistochemical studies were conducted as described above. PGRMC1 is highly expressed in ovarian tumors and even appears to increase in ovarian tumors that no longer express PGR (Compare FIGS. 5B and D with FIGS. 5A and C).

Example 4 siRNA Studies Using SIGC Cells

Figure 6A:
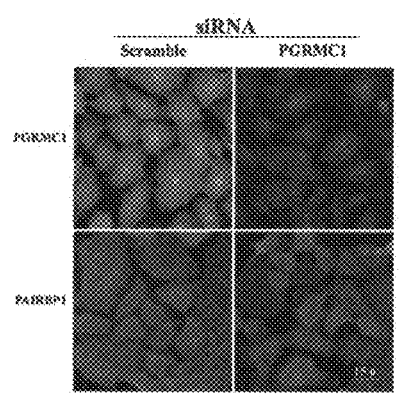
FIG. 6A is a scan of a micrograph showing the effect of PGRMC1 siRNA on the expression of PGRMC1.
Figure 6B:
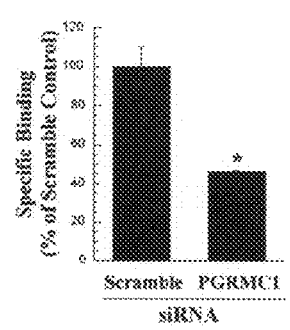
FIG. 6B is a bar graph showing the effect of PGRMC1 siRNA on specific $^3$H-PROGESTERONE binding.
Figure 6C:
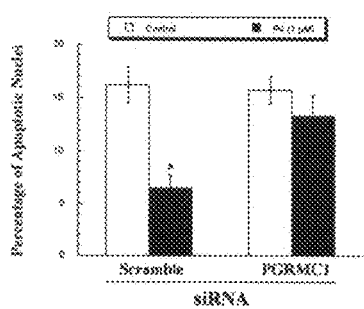
FIG. 6C is a bar graph showing the effect of PGRMC1 siRNA on progesterone's ability to inhibit apoptosis in SIGC cells. The asterisk indicates a value different from control.

Small interfering RNA (siRNA) studies were conducted with Spontaneously Immortalized Granulosa Cells (SIGC). These cells do not express the nuclear Progesterone Receptor (PGR) and therefore do not exhibit the nuclear (genomic) effects of progesterone. The SIGC cells do exhibit the non-genomic effects of progesterone thought to be mediated by the progesterone plasma membrane receptor complex. The cells and the methods for culturing them are described by Peluso et al., *Endocrinology* 147(6):3133-3140 (2006). The starting point for the conditions for delivery of siRNAs is the protocol provided by Ambion Inc. (Austin, Tex.), the source of the siRNAs used in these experiments. The experiments used the transfection conditions identified in GAPDH siRNA studies (i.e., 7 microliters of NeoFX transfection agent) that were sufficient to eliminate GAPDH levels. Within 24 hours of transfection with 30 nM predesigned PGRMC1 siRNA (Ambion siRNA ID 194475), PGRMC1 levels were virtually eliminated as assessed by immunocytochemistry. Scramble siRNA served as control (compare the amount of green fluorescence in cells treated with scramble siRNA verses PGRMC1 siRNA in FIG. 6A). Moreover, the depletion of PGRMC1 results in a significant decrease in the ability of these cells to specifically bind progesterone (FIG. 6B) and the complete attenuation of progesterone's ability to prevent apoptosis (FIG. 6C).

Example 5

PGRMC1 Mediates Progesterone's Anti-Apoptotic Action Via its Interaction with PAIRBP1

In order to identify the amino acid sequence within PGRMC1 that interacts with PAIRBP1, a GFP-PGRMC1 deletion series was generated. The numbers associated with each mutant denote the amino acids they encode as shown (FIGS. 7B and 7C). The wild-type (1-194) PGRMC1 and its GFP-PGRMC1 mutants were tested for their effects on progesterone's anti-apoptotic action (FIG. 7B) and for the interaction site with PAIRBP1 (FIG. 7C).
While the wild-type (1-194) transduces progesterone's action, deleting any section results in an inability to mediate progesterone's action. Although there are different functional domains throughout PGRMC1 (structural organization of PGRMC1 in FIG. 7A), depletion of the first 20 amino acids leads to a rate of apoptosis that is even greater than the vector alone or the 1-130 mutant.

Example 6

Regulation of Ovarian Cancer Cell Viability and Sensitivity to Cisplatin by PGRMC1

Progesterone (P4) influences ovarian cancer cells by an unknown mechanism. The objective of this set of experiments was to determine whether P4 acts through progesterone receptor membrane component −1 (PGRMC1) in ovarian cancers. Archival tissue and cDNA provided by OriGene were used for expression studies. In vitro experiments were conducted with Ovcar-3 cells. PCR, Western blot, and immunohistochemistry were used to measure expression of PGRMC1 and nuclear progesterone receptor (PGR). PGRMC1's role in regulating the viability of ovarian cancers was assessed by over expressing PGRMC1, depleting PGRMC1 using siRNA and attenuating PGRMC1's action with a blocking antibody. Apoptosis was determined by DAPI staining.

PGRMC1 mRNA increased while PGR mRNA decreased in advanced stages of ovarian cancer. Unlike PGR, PGRMC1 was expressed in virtually every cancer cell within the tumor. A similar relationship between PGRMC1 and PGR was observed in Ovcar-3 cells. In these cells P4 suppressed apoptosis induced by either serum withdrawal or cisplatin (CDDP). Moreover, in the presence of P4 1) over expression of PGRMC1 reduces the effectiveness of CDDP, 2) depletion of PGRMC1 with siRNA enhances the effects of CDDP and 3) PGRMC1 antibody treatment increases the apoptotic response to CDDP.

The findings described below indicate that PGRMC1 plays an important role in promoting ovarian cancer cell viability and that attenuating PGRMC1's action makes the ovarian cancer cells more sensitive to CDDP. These data indicate that: (1) PGRMC1 expression increases in ovarian carcinoma cells relative to normal ovarian cells, particular in later-stage tumors (stages 3-4) and is thus diagnostic of later stage tumors and prognostic of outcome; (2); PGRMC1/PGR ratios can be used for ovarian carcinoma diagnosis, staging, and/or prognosis; and (3) targeted depletion of PGRMC1 can be used as an adjunct to CDDP therapy.

Materials and Methods
Ovarian Cancer Specimens

For these studies, ovarian cancer specimens were either 1) provided by OriGene (Rockville Md.), 2) archival specimens obtained from the Department of Pathology, University of Ct Hlth Ctr, or 3) an ovarian cancer cell line (Ovcar-3 cells) provided by Dr Nellie Auersperg of The University of British Columbia, Canada.

Ovarian cancer I qPCR tissue arrays were purchased from OriGene and used to assess the expression of PGR and PGRMC1. This array consisted of cDNA obtained from 48 ovarian cancers. All the clinical information associated with each of these samples can be found on the OriGene web site (Ovarian cancer panel 1).

To determine the localization and number of cells that express PGR and PGRMC1, twenty archival specimens were obtained from the Department of Pathology. These specimens were all serous carcinomas and were either Stage Ia (n=2), Stage Ic (n=2), Stage IIc (n=2), Stage IIIb (n=1), Stage IIIc (12) and Stage V (n=1) tumors. Sections from these tumors were immunostained for either PGR or PGRMC1. These specimens were obtained with IRB approval.

In order to assess the effects of CDDP, P4 and PGRMC1's role in regulating the viability of ovarian cancer cells, Ovcar-3 cells were used. Ovcar-3 cells were maintained in culture as described by Kim et al (23). Briefly, Ovcar-3 cells were cultured in RPMI-1640 medium (Invitrogen, Grand Island, N.Y.) supplemented with 10% fetal bovine serum (HyClone, Logan, Utah), 100 U/ml penicillin G, 100 ug/ml streptomycin (Invitrogen, Grand Island, N.Y.), at 37° C. in a humidified atmosphere of 5% $CO_2$ incubator. The Ovcar-3 cells were cultured for 72 hours before each experiment.
Expression of PGR and PGRMC1

Several techniques were used to monitor the expression of PGR and PGRMC1. These include real time PCR, RT-PCR, immunohistochemistry, immunocytochemistry and western blot analysis.

Real Time PCR. Quantitative measurements of PGR and PGRMC1 mRNA were made on cDNA samples provided by OriGene. Briefly, primers to human progesterone receptor (PGR) and human progesterone receptor membrane component 1 (PGRMC-1) were designed using ABI Prism Primer Express 2.0 software (Applied Biosystems, Foster City, Calif.). Primers were evaluated with NCBI blast to confirm product specificity and products were designed to cross intron/exon borders. Primers used were: PGR forward 5'-CATGGTCCTTGGAGGTCGAA-3' (SEQ ID NO: 13) and reverse 5'-GAGAGCAACAGCATCCAGTGC-3' (SEQ ID NO: 14) and PGRMC-1 forward 5'-CAACGGCAAGGT-GTTCGAT-3' (SEQ ID NO: 15) and reverse 5'TCCAG-CAAAGACCCCATACG-3' (SEQ ID NO: 16).

Quantitative real time PCR was performed on the MyiQ Single-Color Real-Time PCR Detection System (Bio-Rad, Hercules, Calif.). Samples were resuspended in twenty-five µl of the iQ SyberGreen Supermix (Bio-Rad) containing appropriate primers. Relative gene expression was evaluated with Bio-Rad iQ5 software using the $\Delta C_T$ method (24). Each gene was evaluated on two separate identical array plates, which were loaded with equal amounts of cDNA per well as described by the manufacturer. End products were also run on agarose gels to confirm product size.

RT-PCR. RT-PCR was used to characterize the expression of PGR and PGRMC1 in Ovcar-3 cells. In this protocol, total RNA was isolated from Ovcar-3 cells using RNeasy Plus MiniKit (Qiagen, Valencia, Calif.). Then cDNA was synthesized by incubating 1 µg of RNA with oligo-dT and M-MLV reverse transcriptase (Invitrogen). Primers for the subsequent PCR reaction were as follows: PGR, forward 5'GTGCAAG-GTTGGAGACAGCT (SEQ ID NO: 17) and reverse 3'-TTTGCCCTTCAGAAGCGGAC (SEQ ID NO: 18) (213 bp); PGRMC1, forward 5'-GAGGATGTGGTGGCGACT (SEQ ID NO: 19) and reverse 3'-TAATCATTTTTC-CGGGCACT (SEQ ID NO: 20) (578 bp). As a positive control for PGR, mRNA isolated from granulosa/luteal cells obtained from patients undergoing IVF was used. The protocol involving the use of these cells was approved by the IRB as previously published (25).

Immunological detection of PGR and PGRMC1. PGR and PGRMC1 were localized in 5 µm paraffin sections of formalin-fixed ovarian tumors. To block endogenous peroxidase activity sections were incubated in 0.3% peroxidase in methanol for 30 min at room temperature. To reduce non-specific staining, the slides were incubated with Powerblock (Biogenex, San Roman, Calif.).

PGR was detected by incubating the PGR antibody (1:50 dilution Ab-8, Lab Vision/Neomarker, Fremont, Calif.) overnight. The epitope for PGR antibody is the N-terminal half of the human PGR. It is a mouse monoclonal antibody that detects both the A and B forms of PGR. After incubation with either the PGR antibody or IgG (negative control), the sections were incubated with biotinylated goat anti-mouse IgG followed by a 30 min incubation with ABC reagent (Vector Laboratories, Burlingame, Calif.). The slides were then developed using a diaminobenzidine-peroxidase substrate for 5 min followed by light counter-staining with Methyl Green. The presence of PGR was revealed by the presence of a reddish-brown precipitate.

Immunohistochemistry and immunocytochemistry were also used to assess the localization of PGRMC1 in formalin-fixed paraffin-embedded tissue sections of ovarian cancers and Ovcar-3 cells, respectively. The Ovcar-3 cells were plated on coverslips that were placed in 35 mm culture dishes, cultured for three days, fixed with 10% formalin and then incubated with 0.1% Triton-X. The PGRMC1 antibody used to stain the tissue sections and cells was a rabbit antibody built against 15 N-terminal amino acids of porcine PGRMC1 (26, 27). This antibody was previously used to detect PGRMC1 in human granulosa/luteal cells (25). The tissue sections and coverslips were incubated overnight at 4° C. with the antibody to PGRMC1 (1:50). After washing to remove the primary antibody, the slides/coverslips were incubated for 1 h at room temperature in the dark with either biotinylated goat anti-rabbit IgG followed by a 30 min incubation with ABC reagent (Vector Laboratories, Burlingame, Calif.) or Alexa Fluor 488-goat anti-rabbit IgG (1:100). Negative controls were also processed as previously described. The slides and coverslips were then observed under bright field, epi-flourescent or confocal optics depending on the experimental design.

For western blot studies, Ovcar-3 cells were lysed in RIPA buffer (50 mM TRIS, 150 mM sodium chloride, 1.0 mM EDTA, 1% Nonidet P40 and 0.25% sodium-deoxycolate; pH 7.0), which was supplemented with complete protease inhibitor cocktail (Roche, Mannheim, Germany) and phosphatase inhibitor cocktail 1 (Sigma Chemical Co., St Louis, Mo.). The lysate was then centrifuged at 1,000×g at 4° C. for 5 min. Aliquots of this preparation were run on a 10% acrylamide gel and transferred to nitrocellulose. The nitrocellulose was then incubated with 5% non-fat dry milk overnight at 4° C. The nitrocellulose blot was then incubated with the rabbit PGRMC1 antibody (1:2000) (25) for 1 h at room temperature. Western blots were processed using a horseradish peroxidase goat anti-rabbit antibody (1:5,000). ECL Western Blotting Analysis System (Amersham Biosciences, Pisataway, N.J.) was used to reveal PGRMC1. As a negative control, rabbit IgG was used in place of the PGRMC1 antibody. Western blot were also conducted using GFP (1:2000; Cell Signaling Inc.) and GAPDH antibodies (1:4000; Ambion Inc.) according to the manufacturer's instructions.

In Vitro Modulation of PGRMC1 Levels in Ovcar-3 Cells

Three approaches were used to alter the levels or activity of PGRMC1. They include over expression, depletion using PGRMC1 siRNA and interference with PGRMC1's activity using a blocking antibody.

In order to increase the levels of PGRMC1, Ovcar-3 cells were transfected with a GFP-PGRMC1 expression vector using a lipofetamine-based protocol as previously described (28). This construct was made by cloning the entire coding region of human PGRMC1 into the pEGFP-N1 vector. This construct was provided by Drs. Wehling and Losel of the University of Heidleburg.

PGRMC1 siRNA treatment was used to deplete PGRMC1 levels (28). In this protocol, PGRMC1 depletion was performed by transfecting PGRMC1 siRNA using siPORT NeoFX transfection protocol outlined by Ambion. Studies were conducted in which either scramble (control) siRNA (Cat#: AM4611) or one of three pre-designed human PGRMC1 siRNAs (Ambion siRNA ID#: 18430, 18340, 18248) were transfected at a concentration of 30 nM. Levels of PGRMC1 mRNA and protein were assessed by real-time PCR and western blot, respectively as previously described. In addition and immunocytochemical analysis confirmed that PGRMC1 siRNA (ID#: 18248) was an effective PGRMC1 siRNA. This siRNA targeted Exon 1 of PGRMC1 (forward, 5'-GGUGUUCGAUGUGACCAAAtt and reverse, 5'-UUUGGUCACAUCGAACACCtt). Based on this, Ovcar-3 cells were cultured for 3 days and then treated for 3 days with either scramble or PGRMC1 siRNA (ID#: 18248). The cells were then treated for 24 h with CDDP (15 µM) and P4 (1 µM) and observed apoptosis as described below.

Finally, a blocking antibody study was conducted as previously described (25). Ovcar-3 were plated and cultured for 3 days as previously described. The cells were then washed and cultured for 24 h with serum-supplemented containing CDDP (15 µM) and P4 (1 µM) and either rabbit IgG (20 µg/ml) or the antibody to PGRMC1 (20 µg/ml). After culture the cells were rinsed in Krebs/Hepes buffer and stained to detect apoptotic nuclei as described below.

Detection of Apoptotic Nuclei

Figure 12:
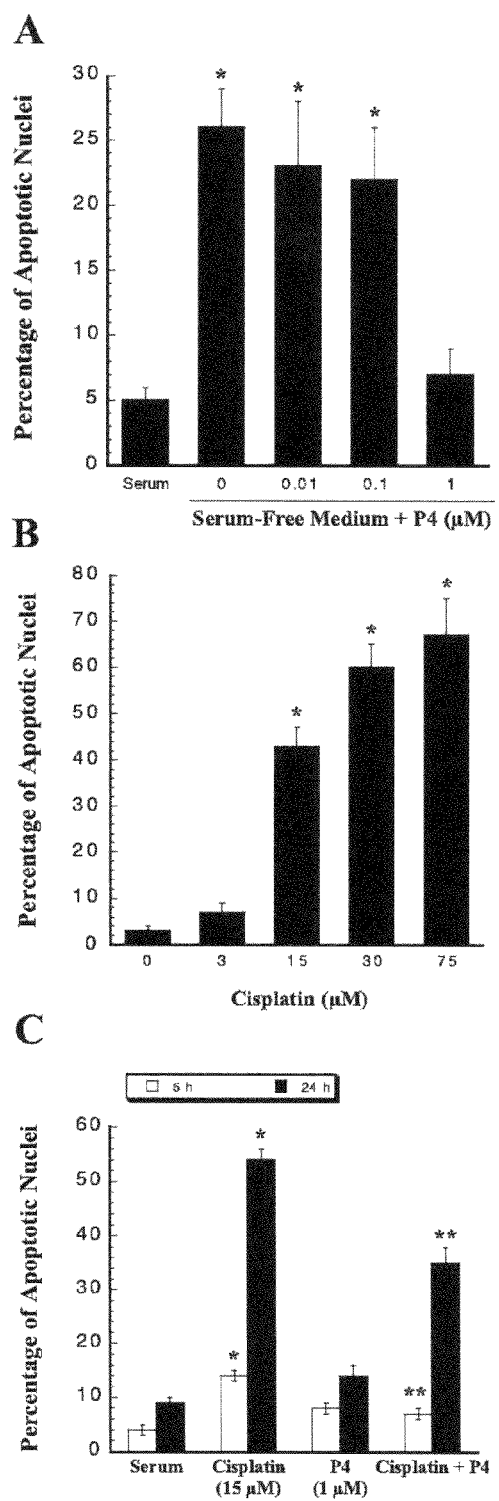
FIG. 12 is a series of graphs showing the effect of progesterone (P4) (A), cisplatin (CDDP) (B) and P4 and CDDP on the percentage of Ovcar-3 cells undergoing apoptosis. Values are expressed as means±one standard error. * indicates a value is different from serum control (p<0.05). ** indicates a value that is less that CDDP treatment (p<0.05).
Figure 15:
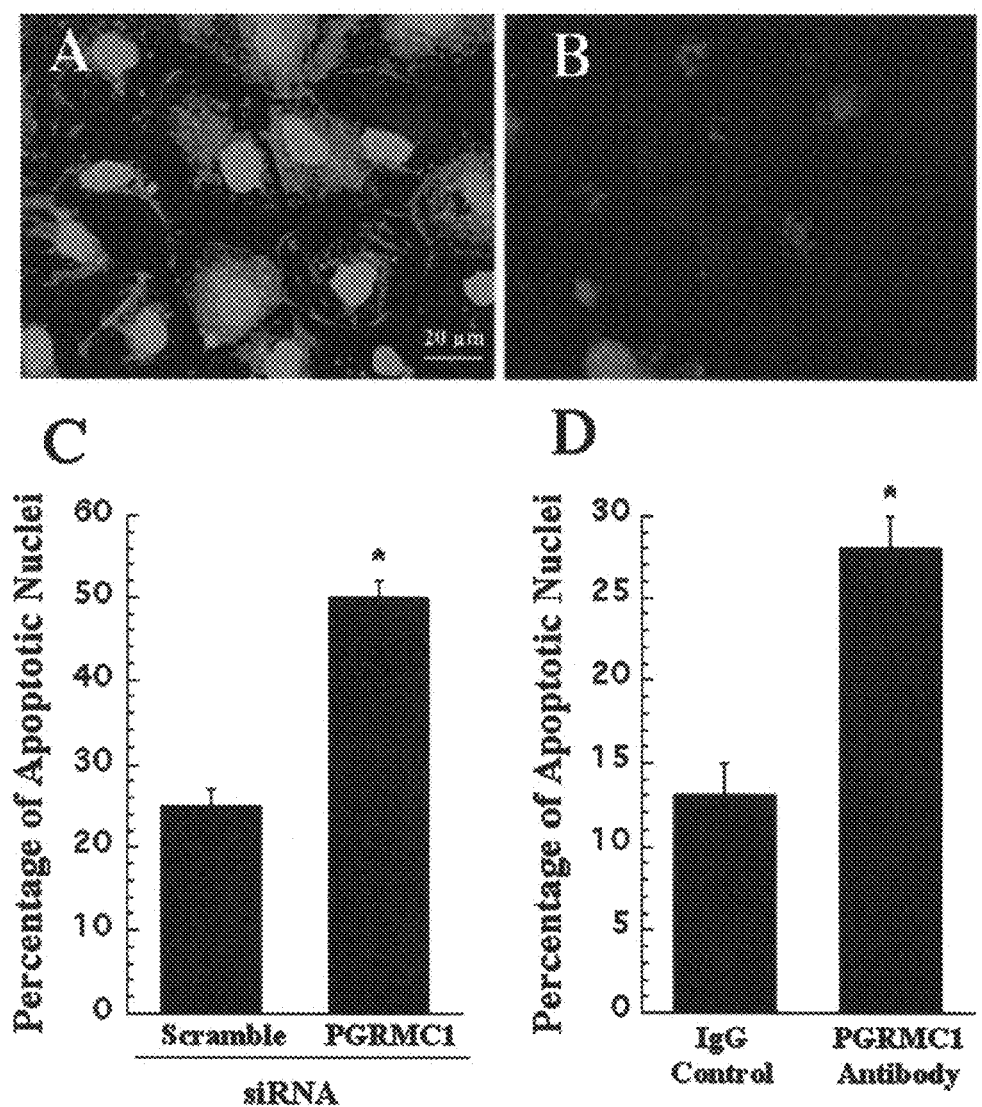
FIG. 15 is a composite of photomicrograph scans and graphs showing immunocytochemical localization of PGRMC1 in Ovcar-3 cells after a 3 day treatment with either scramble control siRNA (A) or PGRMC1 siRNA (ID#: 18248; B). Fluorescence was not observed in the negative controls. The effect of PGRMC1 siRNA treatment on the percentage of Ovcar-3 cells undergoing apoptosis in response to CDDP and P4 is shown in C. In panel D, the effect of PGRMC1 antibody exposure on the percentage of Ovcar-3 cells undergoing apoptosis in response to CDDP and P4 is shown. Values shown in panels C and D represent a mean±standard error and * indicates a value that is different from control (p<0.05).

Regardless of the experimental design, in situ DNA staining was used to identify apoptotic nuclei by adding DAPI directly to the culture medium at a final concentration of 2 µg/ml. The cultures were incubated for 10 min at 37° C. in the dark. After staining, the cells were observed under epi-fluorescent optics. Under these conditions only cells with condensed or fragmented nuclei were stained intensely with DAPI. The DAPI-stained cells also stained with YOPRO-1, a well-known nuclear stain that identifies apoptotic cells (19, 25, 28). These cells were considered to be apoptotic (25). At least 100 cells/culture well were counted and the percentage of apoptotic nuclei in each well determined. For the data shown in FIGS. 12 and 15, cells were selected randomly. In FIG. 6 the apoptotic status (i.e. DAPI staining; blue fluorescence) was determined for 100 transfected cells per well as indicated by their GFP (i.e. green) fluorescence.

Statistical Analysis

All experiments were repeated two to three times. The apoptosis studies were usually conducted in triplicate. When appropriate, the data were pooled to generate means±standard errors and analyzed by either a Student "t" test when an experiment consisted of two treatment groups or a one-way ANOVA followed by a Student-Newman-Keuls test, if more than two treatments groups were being compared. Due to heterogeneity of variance, the PGRMC1/PGR mRNA data was log transformed before analysis. Regardless of the statistical test used, P values of less than 0.05 were considered to be significant.

Results

Figure 8:
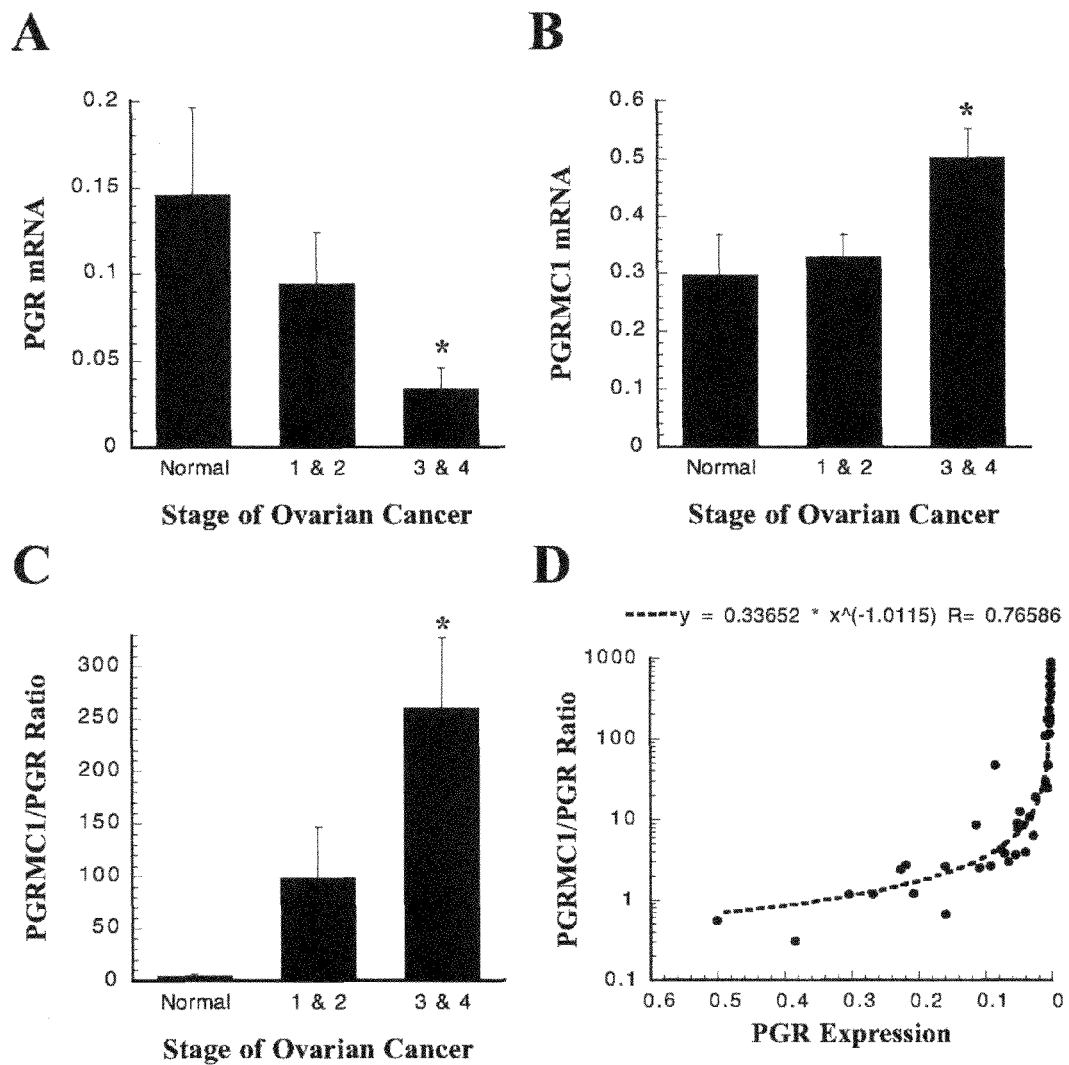
FIG. 8 is a series of graphs showing the effect of the stage of ovarian cancer on the amount of Progesterone Receptor (PGR) mRNA (A) Progesterone Receptor Membrane Component-1 (PGRMC1) mRNA (B), and the ratio of PGRMC1 to PGR mRNA (C). PGRMC1 and PGRMC1 were detected by quantitative real time PCR. In panels A, B and C, mRNA levels were expressed as a mean±one standard error. The correlation between the PGRMC1/PGR mRNA ratios and PGR mRNA levels is shown in panel D.

The mRNA that encodes PGR was detected by real-time PCR in samples of normal ovarian tissue but its abundance decreased with increased stage of ovarian cancer ($p<0.05$; FIG. 8A). PGRMC1 mRNA was also readily detected by real-time PCR in normal ovarian tissue (FIG. 8B), with its level of expression being 2-4 fold greater than that of PGR (FIG. 8C). PGRMC1 mRNA levels remained relatively constant in Stages I and II ovarian cancers and then increased in Stage III-IV ovarian cancers ($p<0.05$; FIG. 8B). As might be predicted, the ratio of PGRMC1 to PGR mRNA increased with advancing stage of ovarian cancer ($<0.05$; FIG. 8C). Moreover when all samples were analyzed, there was an inverse relationship between the PGRMC1 mRNA/PGR mRNA ratio and PGR mRNA levels (FIG. 8D; r=0.76).

Figure 9:
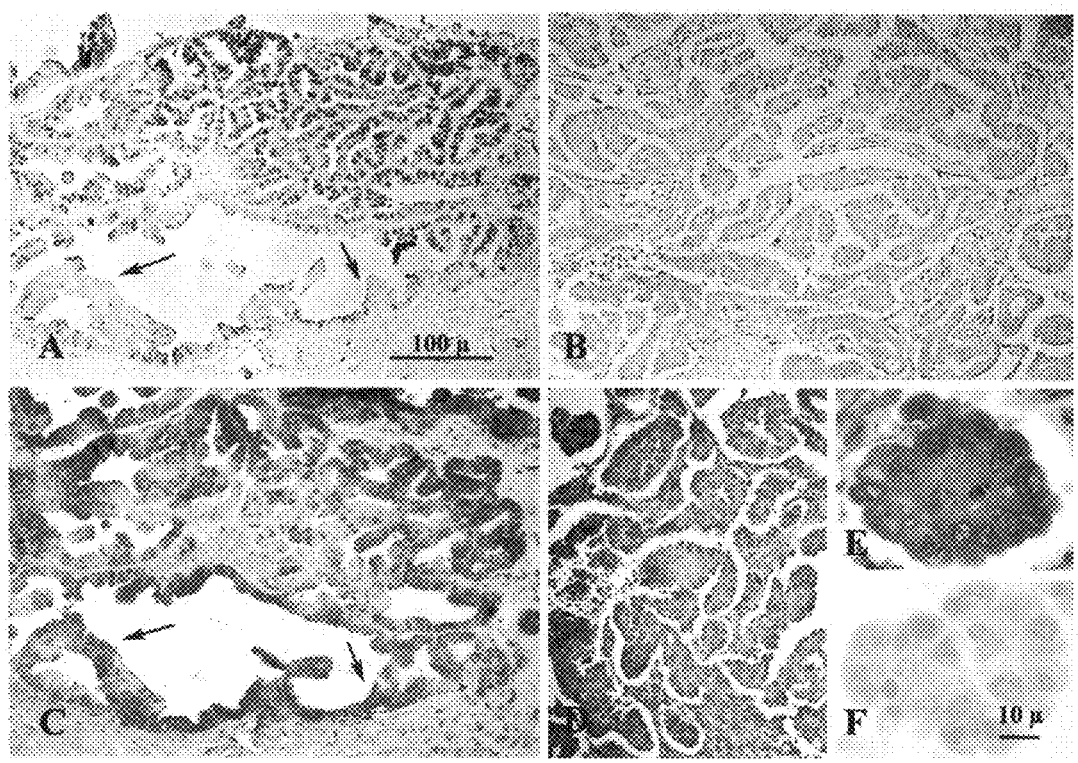
FIG. 9 is a series of scans of photomicrographs showing immunohistochemical localization of Progesterone Receptor (PGR) (A,B) and Progesterone Receptor Membrane Component-1 (PGRMC1) (C,D) in Stage IIIc Grade 2 (A,C) and Stage IIIc Grade 3 (B,D,E) ovarian tumors. Images from panels A and C and B and D are taken from adjacent sections from respective tumors; Panels A, B C and D are shown at the same magnification. The arrows in panels A and C mark the location of ovarian cancer cells that do not express PGR but do express PGRMC1. The image in panel E is a higher magnification of the image shown in panel D. Panel F is a negative control. Both panel E and F are shown at the same magnification. Note that this figure is a modification of FIG. 12 which appeared in a recent review by J J Peluso entitled "Non-genomic actions of progesterone in the normal and neoplastic mammalian ovary" which was published in Seminars in Reprod Med (2007) 25:198-207.
Figure 10:
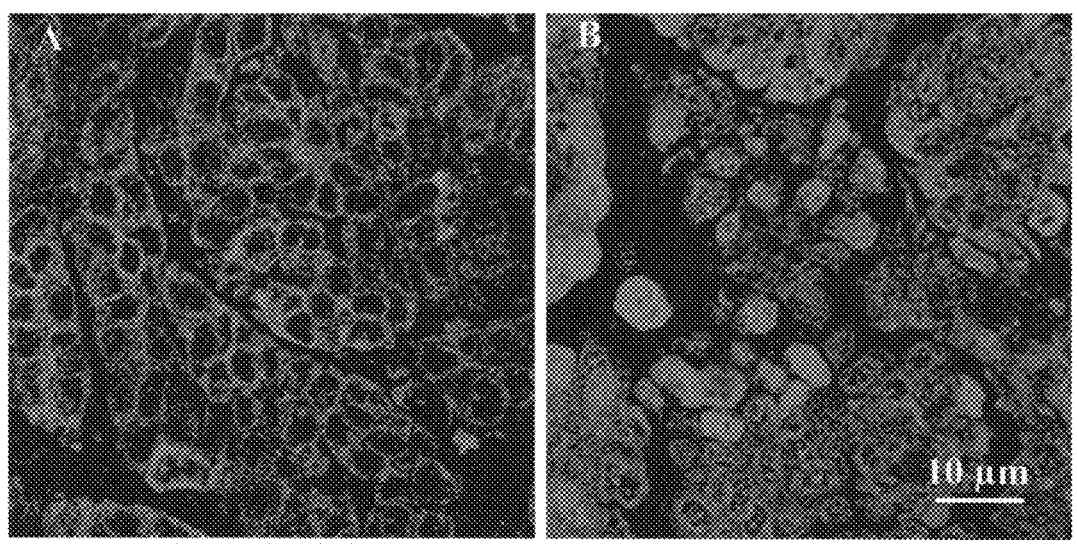
FIG. 10 is a series of scans of photomicrographs showing localization of Progesterone Receptor Membrane Component-1 (PGRMC1) by immunofluorescence and confocal microscopy. Images are shown for Stage Ia (A) and Stage IIc (B) ovarian tumors. Negative controls did not show any fluorescence.

Immunohistochemical analysis confirmed this relationship between PGR and PGRMC1 expression. As seen in FIG. 9A, PGR was expressed by some but not all cells of an ovarian cancer. Moreover, PGR was not detected in all areas of PGR positive tumors. Conversely, PGRMC1 was detected in virtually all of the cells of ovarian tumors (FIG. 9C), even in cells that do not express PGR (compare cells marked with arrows in FIGS. 9A and 9C). In most ovarian cancers PGR was not detected (FIG. 9B), while PGRMC1 was highly expressed (FIG. 9D). In about half the ovarian tumors examined, PGRMC1 was predominately detected in the cytoplasm, while in the remaining tumors PGRMC1 was observed throughout the cell including the nucleus (FIG. 9E). To confirm this observation, the cellular localization of PGRMC1 was assessed using confocal microscopy. This microscopic approach confirmed that PGRMC1 was predominately cytoplasmic in some tumors (FIG. 10A) and localized throughout the cell in others (FIG. 10B). In many of these tumor cells, PGRMC1 appeared to be highly concentrated in the nucleus (FIG. 10B).

Figure 11:
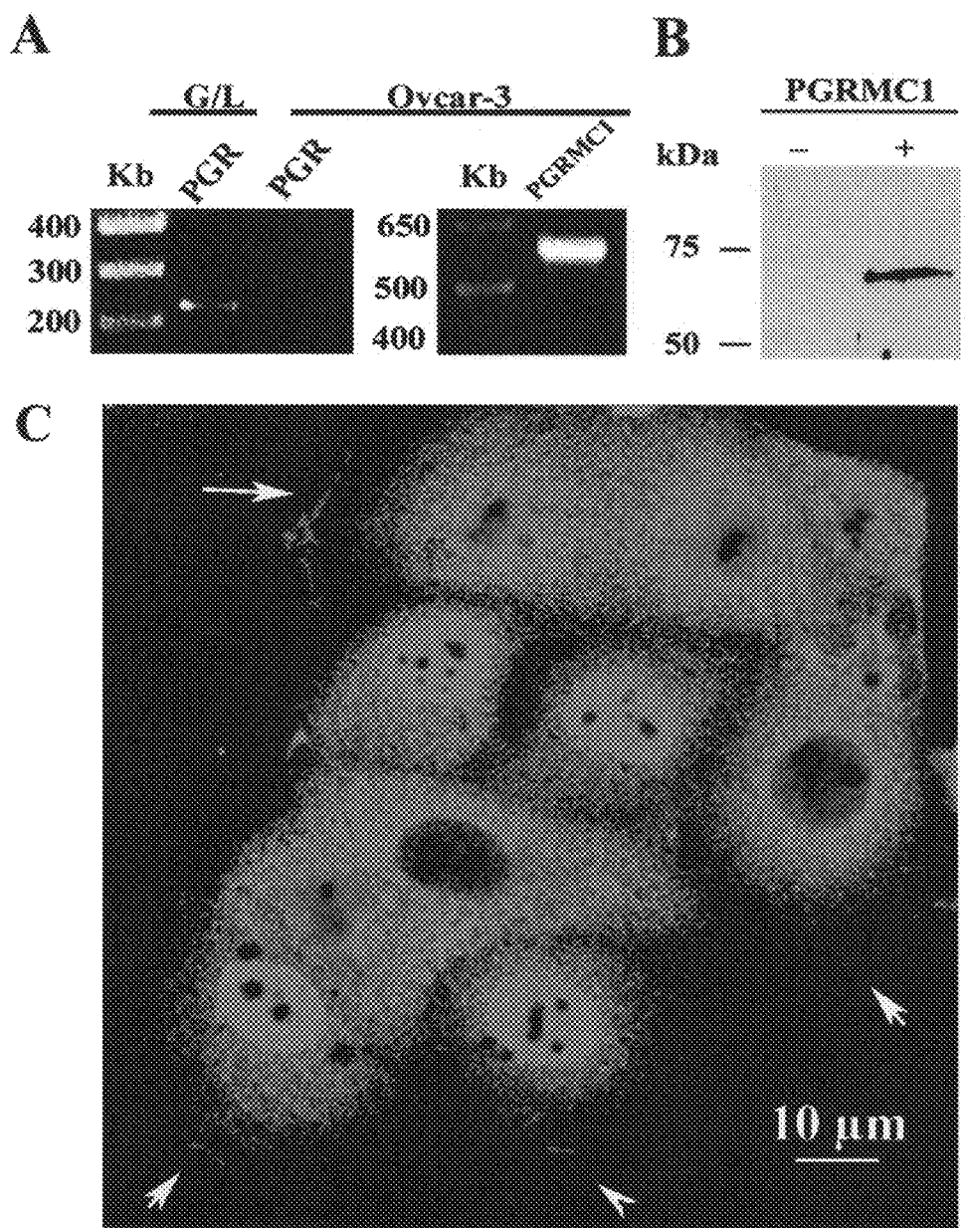
FIG. 11 is a series of scans of RNA gels, a western blot, and a photomicrograph showing expression of Progesterone Receptor (PGR) and Progesterone Receptor Membrane Component-1 (PGRMC1) in Ovcar-3 cells. The presence of mRNA that encodes PGR and PGRMC1 was detected by RT-PCR (A). Note that human granulosa/luteal (G/L) cells were used as a positive control for PGR. Panel B shows a western blot, which detects PGRMC1 as a trimer of approximately 66 kDa. A negative control is also shown in the lane marked by a minus sign. Panel C is a confocal image illustrating that PGRMC1 is localized to the cytoplasm and in some nuclei. PGRMC1 is also localized to select areas of the plasma membrane (marked by arrows).

Ovcar-3 cells were also assessed for the presence of PGR and PGRMC1 mRNA. RT-PCR analysis failed to detect PGR in Ovcar-3 cells but did detect this mRNA in human granulosa/luteal cells (FIG. 11A). The mRNA that encodes PGRMC1 was detectable by RT-PCR in Ovcar-3 cells (FIG. 11A). PGRMC1 expression was also confirmed by western blot as revealed by the presence of a protein band of ≈66 kDa, which likely represents a trimer of the 22 kDa PGRMC1 molecule (FIG. 11B). This assessment is based on the finding that exposure to high concentrations of dithiothreitol is required to disrupt the disulfide bridges that bind monomers of PGRMC1 together (29). PGRMC1 was observed throughout the cytoplasm and nucleus of Ovcar-3 cells (FIG. 11C). PGRMC1 also appeared to be preferentially localized to either the cytoplasm or nucleus depending on the individual cell (FIG. 11C). Finally, PGRMC1 was detected along a limited area of plasma membrane (FIG. 11C).

When Ovcar-3 cells were placed in serum-free media for 5 h, about 25% of the cells underwent apoptosis and this rate of apoptosis was attenuated by P4 treatment ($p<0.05$; FIG. 12A). In the presence of 10% fetal bovine serum, CDDP induced a dose-dependent increase in the percentage of Ovcar-3 cells that undergo apoptosis (FIG. 12B). This effect of CDDP was attenuated at both 5 h ($p<0.05$) and 24 h ($p<0.05$) of culture by simultaneous treatment with P4 (FIG. 12C).

Figure 13:
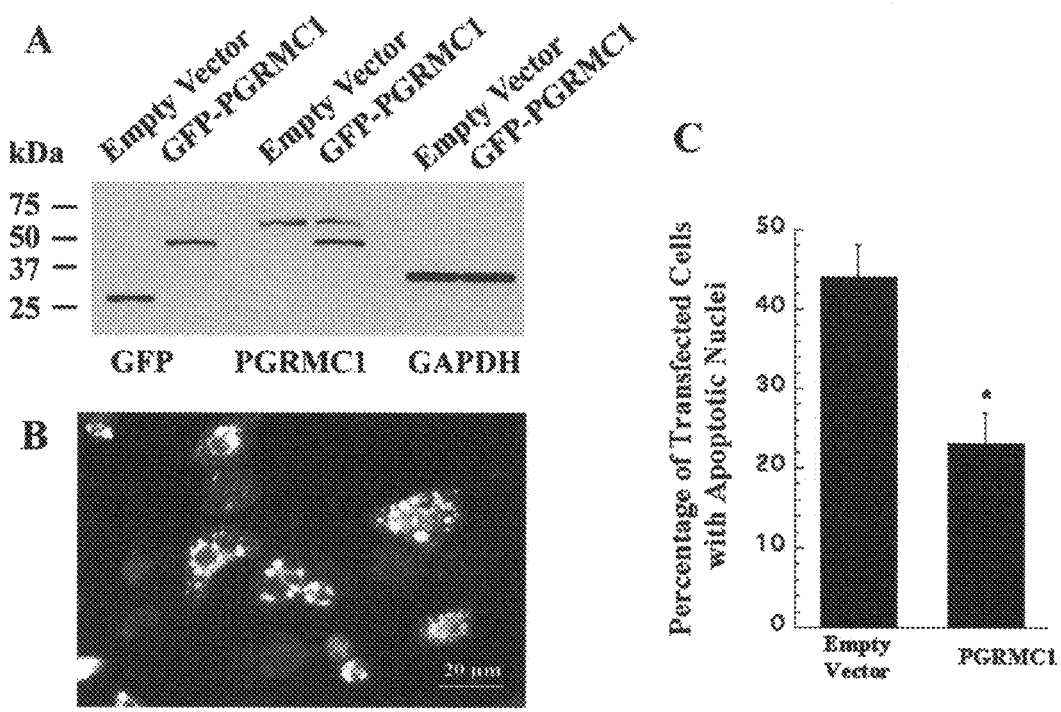
FIG. 13 is a composite of scans of a western blot, a photomicrograph, and a graph showing the effect of over expression of GFP-PGRMC1 on the expression of PGRMC1 and on CDDP-induced apoptosis. Expression was as assessed by western blots probed with either the GFP antibody or the PGRMC1 antibody. A western blot probed with an antibody to GAPDH is shown as a loading control. Note that the endogenous PGRMC1 is detected as a trimer, while the GFP-PGRMC1 is detected as a 50 kDa protein (i.e. 28 kDa GFP plus a 22 kDa PGRMC1 monomer) (A). Negative controls for all of the western blots did not reveal any bands (data not shown). GFP-PGRMC1 is detected in approximately 30% of the cells (B). The effect of GFP-PGRMC1 over expression on the percentage of transfected Ovcar-3 cells undergoing apoptosis in response to CDDP and P4 is shown in C. Values are shown as a mean±standard error and * indicates a value that is different from the empty vector control (p<0.05).

To determine the role of PGRMC1 in mediating P4's anti-apoptotic action, Ovcar-3 cells were transfected with a GFP-PGRMC1 expression vector. As can be seen in FIG. 13A, transfection with the GFP-PGRMC1 vector increased the level of PGRMC1. In addition, GFP-PGRMC1 was expressed in about 30% of the cells (FIG. 13B). In the presence of P4, Ovcar-3 cells transfected with GFP-PGRMC1 were less responsive to the apoptotic effects of CDDP compared to those Ovcar-3 cells transfected with empty GFP vector alone ($p<0.05$; FIG. 13C).

Figure 14:
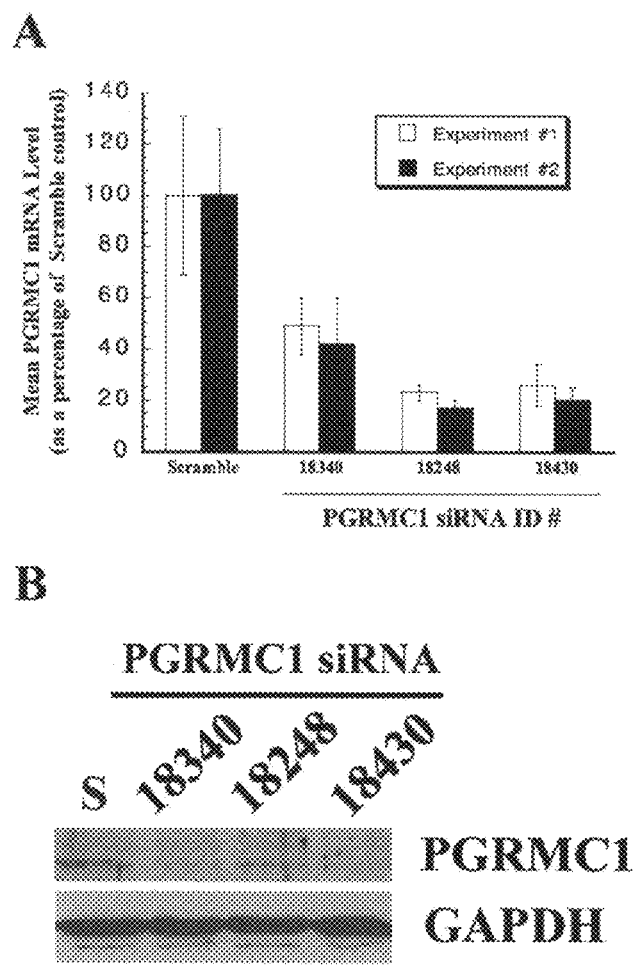
FIG. 14 is a graph and a scan of western blots showing the effect of PGRMC1 siRNA treatment on the levels of PGRMC1 in Ovcar-3 cells as assessed by quantitative real-time PCR (A) and western blot analysis (B). The values in panel A represents triplicate RNA measurements after treatment with either scramble control siRNA or one of three PGRMC1 siRNAs as described in the Materials and Methods section. The results for each experimental replicate are shown in panel A. Representative western blots from this experiment are shown in panel B. The upper blot shows the 66 kDa band associated with PGRMC1, while the lower blot illustrates the levels GAPDH. The lane marked with an S represents a lysate obtained from Ovcar-3 cells treated with Scramble control siRNA.

PGRMC1 levels were also depleted by treatment for 72 h with three different PGRMC1 siRNAs. As seen in FIG. 14A, each of the PGRMC1 siRNA suppressed PGRMC1 mRNA levels compared to the scramble control. Similarly, proteins levels of PGRMC1 were reduced by PGRMC1 siRNA treatment (FIG. 14B). Immunocytochemical analysis after 72 h treatment with either scramble control or PGRMC1 siRNA (ID#: 18248) confirmed the effectiveness of this siRNA treatment to suppress PGRMC1 levels (Compare FIG. 15A with 15B). As might be expected, this PGRMC1 siRNA treatment attenuated P4's ability to inhibit CDDP-induced apoptosis ($p<0.05$; FIG. 15C). Similarly, treatment with PGRMC1 blocking antibody reduced the capacity of P4 to inhibit the apoptotic effects of CDDP (FIG. 15D).

Discussion

The present study is the first to assess the expression pattern of PGRMC1 in human ovarian cancers and to compare its expression with that of PGR. This study demonstrates that PGRMC1 is expressed in early stage ovarian cancers and its expression is increased in more advanced stages. Moreover, PGRMC1 is detected in virtually every ovarian cancer cell regardless of the stage of the tumor. In contrast PGR is expressed in some ovarian cancers and its level is generally depleted in advanced stages. Even when present, PGR is seldom detected in all cells of the tumor.

It is interesting that there exists an inverse relationship between PGR and PGRMC1 expression. This is consistent with the idea that PGR activation suppresses PGRMC1 expression. This concept is supported by the finding that P4 suppresses PGRMC1 levels and that PGRMC1 levels are increased in PGR null mice (30). Although an analysis of the PGRMC1 promoter failed to reveal the presence of a P4 response element, a consensus glucocorticoid response element (GRE) was detected (31). Since P4 can mediate its transcriptional activity through a GRE (32), it is conceivable that ligand activated PGR acting through the GRE could antagonize the expression of PGRMC1. Therefore, the protective effect of P4 may be due in part to PGR mediated suppression of PGRMC1, since lowering the levels of PGRMC1 would increase the sensitivity of ovarian cancer cells to CDDP.

In all ovarian cancer cells PGRMC1 localizes to the cytoplasm and plasma membrane, but in some of these cells PGRMC1 appears to concentrate in the nucleus. PGRMC1 is also observed within the nucleus of some Ovcar-3 cells. In Hela cells PGRMC1 has been shown to localize to the nucleus if it is phosphorylated at two sites (Serine 57 and 181) (33). Both of these serines are within consensus Casein Kinase 2 sites. This implies that PGRMC1 localization is highly and precisely regulated possibly through a kinase cascade that involves Casein Kinase 2. The physiological significance of nuclear PGRMC1 is unknown but might reflect a transcriptional function, since our microarray studies indicate that PGRMC1 siRNA treatment alters the mRNA levels of 80 genes more than 1.5 fold. Whether the expression of any of these genes is directly regulated by nuclear PGRMC1 is unknown but this finding is consistent with a proposed transcriptional function for nuclear PGRMC1.

Clearly the ratio of PGRMC1 to PGR is changed in the different stages of cancer and the ratio of these two P4 receptors could change the tumor's response to P4. Interestingly, in vitro studies have shown that P4 affects the growth of ovarian cancer cell lines in a bi-phasic manner (4, 34-36). At low concentrations (i.e. nM) P4 promotes growth while at higher concentrations (μM) P4 inhibits growth and prevents apoptosis (4, 34-36). In cell lines that do not express PGR, the growth promoting actions are not observed (37), suggesting that the proliferative effect of P4 is mediated by PGR. This ability to respond to low levels of P4 is consistent with the PGR's P4 binding characteristics (i.e. $K_d$=1-5 nM) (38) and the findings that ligand activation of PGR stimulates MAP kinase activity and genes that are required for cell proliferation (39). Ironically, the P4-induced increase in proliferation may make the cells more susceptible to CDDP, since CDDP binds to the DNA in mitotic cells (40, 41).

Given the expression pattern of PGR and PGRMC1, it is important to determine P4's effects on ovarian cancer cells where the ratio of PGRMC1 to PGR dramatically increases as it does in more advanced stage ovarian cancers. The present studies demonstrate that P4 treatment of Ovcar-3 that express PGRMC1 but not PGR promotes cell survival and resistance to CDDP. Therefore, determining the ratio of PGRMC1 to PGR mRNA may be useful as a biomarker to predict the ovarian tumor's response to P4 and sensitivity to CDDP.

Although the descriptive observations presented in this paper suggest a role of PGRMC1 in regulating ovarian cancer viability, they do not conclusively demonstrate that PGRMC1 is required for P4's anti-apoptotic action. To establish this causal relationship, the level of PGRMC1 was modulated and P4 responses monitored in a well-characterized human ovarian cancer cell line, Ovcar-3 cells (i.e. Ovcar-3 cells have over 500 citations in the PubMed database). These cells have been shown to be responsive to P4 (34) and previous studies indicate that they express PGR (42). However like ovarian cancers, the receptor status of ovarian cancer cell lines can change. The RT-PCR analysis in the present study failed to detect PGR in the Ovcar-3 cells, which were provided by Dr Nellie Auersperg. RT-PCR analysis did detect PGRMC1. The presence of PGRMC1 was also confirmed by western blot analysis. Because these Ovcar-3 cells express PGRMC1 but not PGR, they mimic the P4 receptor status of more advanced ovarian cancers and thereby serve as a good model to study PGRMC1's role in the more advanced ovarian cancers.

In normal human and rodent ovarian cells, P4 inhibits apoptosis (19, 20, 25, 28). The present studies also show that P4 inhibits Ovcar-3 cells from undergoing apoptosis induced in response to serum withdrawal with a maximum effect in the 1 μM range. While this amount of P4 is higher than that normally observed in serum, ovarian levels of P4 are several fold greater than 1 μM (35). Moreover, ovarian cancer cells can synthesize P4 (7), thus insuring that the ovarian cancer cells are continuously in a high P4 environment. This high P4 environment likely promotes ovarian cancer cell viability and decreases their sensitivity to CDDP. This is supported by the present in vitro studies that demonstrate that CDDP in the presence of serum induces apoptosis in 40 to 60% of the Ovcar-3 cells within 24 h. However the addition of P4 reduces the killing effect of CDDP by about 40%.

That the anti-apoptotic action of P4 in Ovcar-3 cells is mediated by PGRMC1 is supported by three different experimental approaches. First, over expression of PGRMC1, which is known to increase the number of cellular binding sites for $^3$H-P4 (28), reduces the killing effects of CDDP by about 50%. Second, depleting PGRMC1 with siRNA treatment enhances the killing effect of CDDP in the presence of P4 by ≧50%. Third, an antibody to PGRMC1 makes the cells more sensitive to CDDP even in the presence of P4. The observed effect of the antibody treatment is consistent with previous work with normal ovarian cells (19, 25, 28) and implies that P4 triggers an anti-apoptotic signal transduction pathway in part through a membrane-initiated event, as antibodies do not penetrate the cell membrane. However PGRMC1 also localizes to the cytoplasm and nucleus. It is possible then that PGRMC1 may act no only act at the plasma membrane, but also within the cytoplasm and nucleus to regulate several different pathways with each pathway being essential for cell survival. Regardless of the precise site of action, these in vitro studies provide compelling evidence that PGRMC1 promotes ovarian cancer cell viability. More importantly, they also provide a scientific basis for the development of an adjunct therapy for the treatment of ovarian cancers, since both antibodies (43) and more recently siRNAs (44-46) have been used to target specific cancers and/or oncogenic proteins.

In summary, the present study demonstrates that ovarian cancers express PGRMC1 and that its activation promotes the survival of these cells and makes them more resistant to CDDP. These observations indicate that PGRMC1 can be used as a biomarker for diagnosing, staging, and/or prognosing ovarian cancer. Moreover, the finding that either siRNA or PGRMC1 antibody treatment attenuates PGRMC1's actions indicates that these approaches can be used clinically to ablate PGRMC1 and thereby improve the efficiency of CDDP therapy. In addition, PGRMC1 can be used as a drug discovery target to identify therapeutic compounds to treat ovarian cancer.

REFERENCES

All cited publications, patents, patent applications, and sequence information cited by GenBank, Ensembl, or other public sequence database accession numbers are specifically incorporated by reference herein in their entirety. In particular, the following references are hereby incorporated by reference in their entirety.

1. Salzberg M, Thurlimann B, Bonnefois H, Fink D, Rochlitz C, von Moos R, Senn H 2005 Current concepts of treatment strategies in advanced or recurrent ovarian cancer. Oncology 68:293-8
2. Lindgren P, Backstrom T, Mahlck C G, Ridderheim M, Cajander S 2001 Steroid receptors and hormones in relation to cell proliferation and apoptosis in poorly differentiated epithelial ovarian tumors. Int J Oncol 19:31-8
3. Barnes M N, Berry W D, Straughn J M, Kirby T O, Leath C A, Huh W K, Grizzle W E, Partridge E E 2002 A pilot study of ovarian cancer chemoprevention using medroxyprogesterone acetate in an avian model of spontaneous ovarian carcinogenesis. Gynecol Oncol 87:57-63
4. Ho S M 2003 Estrogen, progesterone and epithelial ovarian cancer. Reprod Biol Endocrinol 1:73
5. Lukanova A, Kaaks R 2005 Endogenous hormones and ovarian cancer: epidemiology and current hypotheses. Cancer Epidemiol Biomarkers Prev 14:98-107
6. Juengel J L, Niswender G D 1999 Molecular regulation of luteal progesterone synthesis in domestic ruminants. J Reprod Fertil Suppl 54:193-205
7. Rae M T, Hillier S G 2005 Steroid signalling in the ovarian surface epithelium. Trends Endocrinol Metab 16:327-33
8. Cameron M R, Caudle M R, Sullivan W R, Jr., Peluso J J, Wimalasena J 1995 The steroidogenic and morphological effects of paclitaxel on cultured ovarian cancer cells. Oncol Res 7:145-56
9. Yu S, Lee M, Shin S, Park J 2001 Apoptosis induced by progesterone in human ovarian cancer cell line SNU-840. J Cell Biochem 82:445-51
10. Rodriguez G C, Walmer D K, Cline M, Krigman H, Lessey B A, Whitaker R S, Dodge R, Hughes C L 1998 Effect of progestin on the ovarian epithelium of macaques: cancer prevention through apoptosis? J Soc Gynecol Investig 5:271-6
11. McDonnel A C, Van Kirk E A, Isaak D D, Murdoch W J 2005 Effects of progesterone on ovarian tumorigenesis in xenografted mice. Cancer Lett 221:49-53
12. Slotman B J, Nauta J J, Rao B R 1990 Survival of patients with ovarian cancer. Apart from stage and grade, tumor progesterone receptor content is a prognostic indicator. Cancer 66:740-4
13. Hempling R E, Piver M S, Eltabbakh G H, Recio F O 1998 Progesterone receptor status is a significant prognostic variable of progression-free survival in advanced epithelial ovarian cancer. Am J Clin Oncol 21:447-51
14. Munstedt K, Steen J, Knauf A G, Buch T, von Georgi R, Franke F E 2000 Steroid hormone receptors and long term survival in invasive ovarian cancer. Cancer 89:1783-91
15. Gabra H, Taylor L, Cohen B B, Lessels A, Eccles D M, Leonard R C, Smyth J F, Steel C M 1995 Chromosome 11 allele imbalance and clinicopathological correlates in ovarian tumours. Br J Cancer 72:367-75
16. Gabra H, Langdon S P, Watson J E, Hawkins R A, Cohen B B, Taylor L, Mackay J, Steel C M, Leonard R C, Smyth J F 1995 Loss of heterozygosity at 11q22 correlates with low progesterone receptor content in epithelial ovarian cancer. Clin Cancer Res 1:945-53
17. Davis M, Hitchcock A, Foulkes W D, Campbell I G 1996 Refinement of two chromosome 11q regions of loss of heterozygosity in ovarian cancer. Cancer Res 56:741-4
18. Chen X, Feng Y 2003 Effect of progesterone combined with chemotherapy on epithelial ovarian cancer. Chin Med J (Engl) 116:388-91
19. Peluso J J, Pappalardo A, Losel R, Wehling M 2006 Progesterone membrane receptor component 1 expression in the immature rat ovary and its role in mediating progesterone's antiapoptotic action. Endocrinology 147:3133-40
20. Peluso J J, Pappalardo A, Losel R, Wehling M 2005 Expression and function of PAIRBP1 within gonadotropin-primed immature rat ovaries: PAIRBP1 regulation of granulosa and luteal cell viability. Biol Reprod 73:261-70
21. Crudden G, Chitti R E, Craven R J 2006 Hpr6 (heme-1 domain protein) regulates the susceptibility of cancer cells to chemotherapeutic drugs. J Pharmacol Exp Ther 316:448-55
22. Crudden G, Loesel R, Craven R J 2005 Overexpression of the cytochrome p450 activator hpr6 (heme-1 domain protein/human progesterone receptor) in tumors. Tumour Biol 26:142-6
23. Kim K Y, Choi K C, Park S H, Chou C S, Auersperg N, Leung P C 2004 Type II gonadotropin-releasing hormone stimulates p38 mitogen-activated protein kinase and apoptosis in ovarian cancer cells. J Clin Endocrinol Metab 89:3020-6
24. Livak K J, Schmittgen T D 2001 Analysis of relative gene expression data using real-time quantitative PCR and the 2(-Delta Delta C(T)) Method. Methods 25:402-8
25. Engmann L, Losel R, Wehling M, Peluso J J 2006 Progesterone regulation of human granulosa/luteal cell viability by an RU486-independent mechanism. J Clin Endocrinol Metab 91:4962-8
26. Losel R, Breiter S, Seyfert M, Wehling M, Falkenstein E 2005 Classic and non-classic progesterone receptors are both expressed in human spermatozoa. Horm Metab Res 37:10-4
27. Losel R, Dorn-Beineke A, Falkenstein E, Wehling M, Feuring M 2004 Porcine spermatozoa contain more than one membrane progesterone receptor. Int J Biochem Cell Biol 36:1532-41
28. Peluso J J, Romak J, Liu X 2008 Progesterone Receptor Membrane Component-1 (PGRMC1) is the Mediator of Progesterone's Anti-apoptotic Action in Spontaneously Immortalized Granulosa Cells as Revealed by PGRMC1 siRNA Treatment and Functional Analysis of PGRMC1 Mutations. Endocrinology 149: 534-543.
29. Falkenstein E, Eisen C, Schmieding K, Krautkramer M, Stein C, Losel R, Webling M 2001 Chemical modification and structural analysis of the progesterone membrane binding protein from porcine liver membranes. Mol Cell Biochem 218:71-9
30. Krebs C J, Jarvis E D, Chan J, Lydon J P, Ogawa S, Pfaff D W 2000 A membrane-associated progesterone-binding protein, 25-Dx, is regulated by progesterone in brain regions involved in female reproductive behaviors. Proc Natl Acad Sci USA 97:12816-21
31. Bernauer S, Wehling M, Gerdes D, Falkenstein E 2001 The human membrane progesterone receptor gene: genomic structure and promoter analysis. DNA Seq 12:13-25
32. Beato M, Chalepakis G, Schauer M, Slater E P 1989 DNA regulatory elements for steroid hormones. J Steroid Biochem 32:737-47
33. Beausoleil S A, Jedrychowski M, Schwartz D, Elias J E, Villen J, Li J, Cohn M A, Cantley L C, Gygi S P 2004 Large-scale characterization of HeLa cell nuclear phosphoproteins. Proc Natl Acad Sci USA 101:12130-5
34. Fauvet R, Dufournet Etienne C, Poncelet C, Bringuier A F, Feldmann G, Darai E 2006 Effects of progesterone and anti-progestin (mifepristone) treatment on proliferation and apoptosis of the human ovarian cancer cell line, OVCAR-3. Oncol Rep 15:743-8
35. Keith Bechtel M, Bonavida B 2001 Inhibitory effects of 17beta-estradiol and progesterone on ovarian carcinoma cell proliferation: a potential role for inducible nitric oxide synthase. Gynecol Oncol 82:127-38
36. Seeger H, Wallwiener D, Mueck A O 2006 Is there a protective role of progestogens on the proliferation of human ovarian cancer cells in the presence of growth factors? Eur J Gynaecol Oncol 27:139-41
37. Syed V, Ulinski G, Mok S C, Yiu G K, Ho S M 2001 Expression of gonadotropin receptor and growth responses to key reproductive hormones in normal and malignant human ovarian surface epithelial cells. Cancer Res 61:6768-76
38. Stouffer R L 2003 Progesterone as a mediator of gonadotrophin action in the corpus luteum: beyond steroidogenesis. Hum Reprod Update 9:99-117
39. Lange C A 2004 Making sense of cross-talk between steroid hormone receptors and intracellular signaling pathways: who will have the last word? Mol Endocrinol 18:269-78
40. Cepeda V, Fuertes M A, Castilla J, Alonso C, Quevedo C, Perez J M 2007 Biochemical mechanisms of cisplatin cytotoxicity. Anticancer Agents Med Chem 7:3-18
41. Horvath V, Soucek K, Svihalkova-Sindlerova L, Vondracek J, Blanarova O, Hofmanova J, Sova P, Kozubik A 2007 Different cell cycle modulation following treatment of human ovarian carcinoma cells with a new platinum(IV) complex vs cisplatin. Invest New Drugs 25:435-43
42. Akahira J, Suzuki T, Ito K, Kaneko C, Darnel A D, Moriya T, Okamura K, Yaegashi N, Sasano H 2002 Differential expression of progesterone receptor isoforms A and B in the normal ovary, and in benign, borderline, and malignant ovarian tumors. Jpn Cancer Res 93:807-15
43. Crowther M E, Britton K E, Granowska M, Shepherd J H 1989 Monoclonal antibodies and their usefulness in epithelial ovarian cancer. A review. Br J Obstet Gynaecol 96:516-21
44. Racz Z, Hamar P 2006 Can siRNA technology provide the tools for gene therapy of the future? Curr Med Chem 13:2299-307
45. Morris K V 2006 Therapeutic potential of siRNA-mediated transcriptional gene silencing. Biotechniques Suppl: 7-13
46. Xie F Y, Woodle M C, Lu P Y 2006 Harnessing in vivo siRNA delivery for drug discovery and therapeutic development. Drug Discov Today 11:67-73
47. Peluso J J 2007 Non-genomic actions of progesterone in the normal and neoplastic mammalian ovary. Semin Reprod Med 25:198-207
48. Peluso et al., "Progesterone Membrane Receptor Component 1 Expression in the Immature Rat Ovary and Its Role in Mediating Progesterone's Antiapoptotic Action", Endocrinology 147(6):3133-3140 (2006).
49. Peluso, "Multiplicity of Progesterone's Actions and Receptors in the Mammalian Ovary", Biology of Reproduction 75:2-8 (2006).
50. Peluso et al., "Expression and Function of PAIRBP1 Within Gonadotropin-Primed Immature Rate Ovaries: PAIRBP1 Regulation of Granulosa and Luteal Cell Viability", Biology of Reproduction 73:261-270 (2005).
51. Peluso et al., "Involvement of an Unnamed Protein, RDA288, in the Mechanism through which Progesterone Mediates Its Antiapoptotic Action in Spontaneously Immortalized Granulosa Cells", Endocrinology 145(6): 3014-3022 (2004).
52. Chaffkin et al., "The Role of Progesterone in Regulating Human Granulosa Cell Proliferation and Differentiation in Vitro." J Clin Endocrinol Metab 76(3):696-700 (1993).
53. Chaffkin et al., "Progesterone as an Autocrine/Paracrine Regulator of Human Granulosa Cell Proliferation", J Clin Endocrinol Metab 75(6):1404-1408 (1992).
54. Engmann et al., "Progesterone Regulation of Human Granulosa/Luteal Cell Viability by an RU486-Independent Mechanism" J Clin Endocrinol Metab 91(12): 4962-4968 (2006).
55. Losel et al., "Classic and Non-Classic Progesterone Receptors Are Both Expressed in Human Spermatozoa" Horm. Metab. Res. 37: 0-4 (2005).

What is claimed is:

1. A method of identifying an ovarian carcinoma that is at least partially resistant to platinum-based chemotherapy in an individual, comprising testing a sample from the individual for an increased level of Progesterone Receptor Membrane Component-1 (PGRMC1) relative to a level of PGRMC1 in a control sample from an individual having an ovarian carcinoma that responds to platinum-based chemotherapy, whereby the increased level of PGRMC1 identifies an ovarian carcinoma that is at least partially resistant to platinum-based chemotherapy.

2. The method of claim 1, wherein detection of a level of PGRMC1 that is not increased relative to the control sample indicates an ovarian cancer that is sensitive to platinum-based chemotherapy.

3. The method of claim 1, wherein the sample is a tumor sample, a tissue section, cells, blood, urine, sputum, a nucleic acid sample, or a protein sample.

4. The method of claim 1, wherein the level of PGRMC1 is detected by detecting PGRMC1 mRNA in the sample.

5. The method of claim 1, wherein the level of PGRMC1 is detected by detecting PGRMC1 protein in the sample.

* * * * *